US010660370B2

(12) United States Patent
Rogers et al.

(10) Patent No.: US 10,660,370 B2
(45) Date of Patent: May 26, 2020

(54) AEROSOL DELIVERY DEVICE INCLUDING A CONTROL BODY, AN ATOMIZER BODY, AND A CARTRIDGE AND RELATED METHODS

(71) Applicant: RAI STRATEGIC HOLDINGS, INC., Winston-Salem, NC (US)

(72) Inventors: James William Rogers, Cornelius, NC (US); Noah Mark Minskoff, Palo Alto, CA (US)

(73) Assignee: RAI STRATEGIC HOLDINGS, INC., Winston-Salem, NC (US)

(*) Notice: Subject to any disclaimer, the term of this patent is extended or adjusted under 35 U.S.C. 154(b) by 138 days.

(21) Appl. No.: 15/782,543

(22) Filed: Oct. 12, 2017

(65) Prior Publication Data

US 2019/0110517 A1   Apr. 18, 2019

(51) Int. Cl.
| | |
|---|---|
| A24F 11/00 | (2006.01) |
| A24F 47/00 | (2020.01) |
| A24F 13/00 | (2006.01) |
| A24F 17/00 | (2006.01) |
| A24F 25/00 | (2006.01) |
| A61M 11/04 | (2006.01) |
| A61M 15/00 | (2006.01) |
| A61M 15/06 | (2006.01) |

(Continued)

(52) U.S. Cl.
CPC .............. *A24F 47/008* (2013.01); *A24F 1/00* (2013.01); *A61M 11/042* (2014.02); *A61M 15/00* (2013.01); *A61M 15/06* (2013.01); *H05B 3/46* (2013.01); *A61M 2205/8206* (2013.01); *A61M 2207/00* (2013.01)

(58) Field of Classification Search
CPC ................................. A24F 47/008; H05B 3/46
USPC .................................................. 131/328, 329
See application file for complete search history.

(56) References Cited

U.S. PATENT DOCUMENTS

| | | | |
|---|---|---|---|
| 1,514,682 A | 11/1924 | Wilson | |
| 1,771,366 A | 7/1930 | Wyss et al. | |
| 2,057,353 A | 10/1936 | Whittemore, Jr. | |

(Continued)

FOREIGN PATENT DOCUMENTS

| | | |
|---|---|---|
| AU | 276250 | 7/1965 |
| CA | 2 641 869 | 5/2010 |

(Continued)

OTHER PUBLICATIONS

International Search Report dated Jan. 30, 2019 in International Patent Application No. PCT/IB2018/057887 filed Oct. 11, 2018.

*Primary Examiner* — Abdullah A Riyami
*Assistant Examiner* — Thang H Nguyen
(74) *Attorney, Agent, or Firm* — Womble Bond Dickinson (US) LLP

(57) ABSTRACT

The present disclosure relates to aerosol delivery devices. The aerosol delivery devices may include a control body, an atomizer body including an atomizer, and a cartridge including a reservoir configured to contain an aerosol precursor composition. The control body may be configured to releasably engage the atomizer body and the atomizer body may be configured to releasably engage the cartridge. The atomizer may be configured to receive an electrical current from the control body and the aerosol precursor composition from the cartridge to produce an aerosol.

25 Claims, 28 Drawing Sheets
(23 of 28 Drawing Sheet(s) Filed in Color)

(51) Int. Cl.
*A24F 1/00* (2006.01)
*H05B 3/46* (2006.01)

(56) References Cited

U.S. PATENT DOCUMENTS

| | | | |
|---|---|---|---|
| 2,104,266 A | 1/1938 | McCormick | |
| 3,200,819 A | 8/1965 | Gilbert | |
| 3,479,561 A | 11/1969 | Janning | |
| 4,284,089 A | 8/1981 | Ray | |
| 4,303,083 A | 12/1981 | Burruss, Jr. | |
| 4,735,217 A | 4/1988 | Gerth et al. | |
| 4,848,374 A | 7/1989 | Chard et al. | |
| 4,907,606 A | 3/1990 | Lilja et al. | |
| 4,922,901 A | 5/1990 | Brooks et al. | |
| 4,945,931 A | 8/1990 | Gori | |
| 4,947,874 A | 8/1990 | Brooks et al. | |
| 4,947,875 A | 8/1990 | Brooks et al. | |
| 4,986,286 A | 1/1991 | Roberts et al. | |
| 5,019,122 A | 5/1991 | Clearman et al. | |
| 5,042,510 A | 8/1991 | Curtiss et al. | |
| 5,060,671 A | 10/1991 | Counts et al. | |
| 5,093,894 A | 3/1992 | Deevi et al. | |
| 5,144,962 A | 9/1992 | Counts et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | McCafferty et al. | |
| 5,388,574 A | 2/1995 | Ingebrethsen et al. | |
| 5,408,574 A | 4/1995 | Deevi et al. | |
| 5,468,936 A | 11/1995 | Deevi et al. | |
| 5,498,850 A | 3/1996 | Das | |
| 5,515,842 A | 5/1996 | Ramseyer et al. | |
| 5,530,225 A | 6/1996 | Hajaligol | |
| 5,564,442 A | 10/1996 | MacDonald et al. | |
| 5,649,554 A | 7/1997 | Sprinkel et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,727,571 A | 3/1998 | Meiring et al. | |
| 5,743,251 A | 4/1998 | Howell et al. | |
| 5,799,663 A | 9/1998 | Gross et al. | |
| 5,819,756 A | 10/1998 | Mielordt | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,053,176 A | 4/2000 | Adams et al. | |
| 6,089,857 A | 7/2000 | Matsuura et al. | |
| 6,095,153 A | 8/2000 | Kessler et al. | |
| 6,125,853 A | 10/2000 | Susa et al. | |
| 6,155,268 A | 12/2000 | Takeuchi | |
| 6,164,287 A | 12/2000 | White | |
| 6,196,218 B1 | 3/2001 | Voges | |
| 6,196,219 B1 | 3/2001 | Hess et al. | |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,772,756 B2 | 8/2004 | Shayan | |
| 6,803,545 B2 | 10/2004 | Blake et al. | |
| 6,854,461 B2 | 2/2005 | Nichols | |
| 6,854,470 B1 | 2/2005 | Pu | |
| 7,117,867 B2 | 10/2006 | Cox et al. | |
| 7,293,565 B2 | 11/2007 | Griffin et al. | |
| 7,513,253 B2 | 4/2009 | Kobayashi et al. | |
| 7,775,459 B2 | 8/2010 | Martens, III et al. | |
| 7,832,410 B2 | 11/2010 | Hon | |
| 7,845,359 B2 | 12/2010 | Montaser | |
| 7,896,006 B2 | 3/2011 | Hamano et al. | |
| 8,127,772 B2 | 3/2012 | Montaser | |
| 8,314,591 B2 | 11/2012 | Terry et al. | |
| 8,365,742 B2 | 2/2013 | Hon | |
| 8,402,976 B2 | 3/2013 | Fernando et al. | |
| 8,499,766 B1 | 8/2013 | Newton | |
| 8,528,569 B1 | 9/2013 | Newton | |
| 8,550,069 B2 | 10/2013 | Alelov | |
| 8,851,081 B2 | 10/2014 | Fernando et al. | |
| 9,717,276 B2* | 8/2017 | Brammer | A61M 15/06 |
| 10,085,485 B2* | 10/2018 | Hunt | A24F 47/008 |
| 10,179,690 B2* | 1/2019 | Sebastian | B01F 15/00889 |
| 2002/0146242 A1 | 10/2002 | Vieira | |
| 2003/0226837 A1 | 12/2003 | Blake et al. | |
| 2004/0118401 A1 | 6/2004 | Smith et al. | |
| 2004/0129280 A1 | 7/2004 | Woodson et al. | |
| 2004/0200488 A1 | 10/2004 | Felter et al. | |
| 2004/0226568 A1 | 11/2004 | Takeuchi et al. | |
| 2005/0016550 A1 | 1/2005 | Katase | |
| 2006/0016453 A1 | 1/2006 | Kim | |
| 2006/0196518 A1 | 9/2006 | Hon | |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2008/0085103 A1 | 4/2008 | Beland et al. | |
| 2008/0092912 A1 | 4/2008 | Robinson et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0095311 A1 | 4/2009 | Hon | |
| 2009/0095312 A1 | 4/2009 | Herbrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0272379 A1 | 11/2009 | Thorens et al. | |
| 2009/0283103 A1 | 11/2009 | Nielsen et al. | |
| 2009/0320863 A1 | 12/2009 | Fernando et al. | |
| 2010/0043809 A1 | 2/2010 | Magnon | |
| 2010/0083959 A1 | 4/2010 | Siller | |
| 2010/0200006 A1 | 8/2010 | Robinson et al. | |
| 2010/0229881 A1 | 9/2010 | Hearn | |
| 2010/0242974 A1 | 9/2010 | Pan | |
| 2010/0307518 A1 | 12/2010 | Wang | |
| 2010/0313901 A1 | 12/2010 | Fernando et al. | |
| 2011/0005535 A1 | 1/2011 | Xiu | |
| 2011/0011396 A1 | 1/2011 | Fang | |
| 2011/0036363 A1 | 2/2011 | Urtsev et al. | |
| 2011/0036365 A1 | 2/2011 | Chong et al. | |
| 2011/0094523 A1 | 4/2011 | Thorens et al. | |
| 2011/0126848 A1 | 6/2011 | Zuber et al. | |
| 2011/0155153 A1 | 6/2011 | Thorens et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0309157 A1 | 12/2011 | Yang et al. | |
| 2012/0042885 A1 | 2/2012 | Stone et al. | |
| 2012/0060853 A1 | 3/2012 | Robinson et al. | |
| 2012/0111347 A1 | 5/2012 | Hon | |
| 2012/0132643 A1 | 5/2012 | Choi et al. | |
| 2012/0227752 A1 | 9/2012 | Alelov | |
| 2012/0231464 A1 | 9/2012 | Yu et al. | |
| 2012/0260927 A1 | 10/2012 | Liu | |
| 2012/0279512 A1 | 11/2012 | Hon | |
| 2012/0318882 A1 | 12/2012 | Abehasera | |
| 2013/0037041 A1 | 2/2013 | Worm et al. | |
| 2013/0056013 A1 | 3/2013 | Terry et al. | |
| 2013/0081625 A1 | 4/2013 | Rustad et al. | |
| 2013/0081642 A1 | 4/2013 | Safari | |
| 2013/0192619 A1 | 8/2013 | Tucker et al. | |
| 2013/0255702 A1 | 10/2013 | Griffith, Jr. et al. | |
| 2013/0306084 A1 | 11/2013 | Flick | |
| 2013/0319439 A1 | 12/2013 | Gorelick et al. | |
| 2013/0340750 A1 | 12/2013 | Thorens et al. | |
| 2013/0340775 A1 | 12/2013 | Juster et al. | |
| 2014/0000638 A1 | 1/2014 | Sebastian et al. | |
| 2014/0053856 A1* | 2/2014 | Liu | A24F 47/008 131/329 |
| 2014/0060554 A1 | 3/2014 | Collett et al. | |
| 2014/0060555 A1 | 3/2014 | Chang et al. | |
| 2014/0096781 A1 | 4/2014 | Sears et al. | |

(56) References Cited

U.S. PATENT DOCUMENTS

| | | | |
|---|---|---|---|
| 2014/0096782 A1 | 4/2014 | Ampolini et al. | |
| 2014/0109921 A1* | 4/2014 | Chen | A24F 47/008 131/273 |
| 2014/0157583 A1 | 6/2014 | Ward et al. | |
| 2014/0209105 A1 | 7/2014 | Sears et al. | |
| 2014/0238396 A1 | 8/2014 | Buchberger | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2014/0283825 A1 | 9/2014 | Buchberger | |
| 2014/0299125 A1 | 10/2014 | Buchberger | |
| 2014/0345631 A1 | 11/2014 | Bowen et al. | |
| 2015/0007838 A1 | 1/2015 | Fernando et al. | |
| 2015/0053217 A1 | 2/2015 | Steingraber et al. | |
| 2015/0335071 A1* | 11/2015 | Brinkley | A61M 15/06 131/328 |
| 2016/0007651 A1* | 1/2016 | Ampolini | A24F 47/008 131/328 |
| 2016/0007654 A1* | 1/2016 | Zhu | A24F 47/008 131/328 |
| 2016/0037826 A1 | 2/2016 | Hearn et al. | |
| 2016/0249684 A1* | 9/2016 | Liu | A24F 47/008 131/328 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | 2015066121 A1 | 5/2015 |
| WO | 2015179292 A1 | 11/2015 |
| WO | 2017149481 A1 | 9/2017 |
| WO | 2017163212 A1 | 9/2017 |

* cited by examiner

```
┌──────────────────────────────────────────────────────────────────┐  ┌─ 702
│ direct an aerosol precursor composition from a reservoir of a    │
│ cartridge out of the cartridge through a valve assembly          │
└──────────────────────────────────────────────────────────────────┘
                                 │
                                 ▼
┌──────────────────────────────────────────────────────────────────┐  ┌─ 704
│        receive the aerosol precursor composition in an atomizer body        │
└──────────────────────────────────────────────────────────────────┘
                                 │
                                 ▼
┌──────────────────────────────────────────────────────────────────┐  ┌─ 706
│  direct the aerosol precursor composition to an atomizer in the atomizer body │
└──────────────────────────────────────────────────────────────────┘
                                 │
                                 ▼
┌──────────────────────────────────────────────────────────────────┐  ┌─ 708
│  direct an electrical current from a control body to the atomizer to produce an │
│                               aerosol                            │
└──────────────────────────────────────────────────────────────────┘
```

FIG. 17 and a cartridge and related methods

BACKGROUND

Field of the Disclosure

The present disclosure relates to aerosol delivery devices such as electronic cigarettes, and more particularly to aerosol delivery devices including an atomizer. The atomizer may be configured to heat an aerosol precursor composition, which may be made or derived from tobacco or otherwise incorporate tobacco, to form an inhalable substance for human consumption.

Description of Related Art

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., and U.S. Pat. App. Pub. No. 2015/0059780 to Davis et al., which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

However, it may be desirable to provide aerosol delivery devices with alternate configurations. Thus, advances with respect to aerosol delivery devices may be desirable.

BRIEF SUMMARY OF THE DISCLOSURE

The present disclosure relates to aerosol delivery devices configured to produce aerosol and which aerosol delivery devices, in some embodiments, may be referred to as electronic cigarettes. In one aspect, an aerosol delivery device is provided. The aerosol delivery device may include a control body, an atomizer body including an atomizer, and a cartridge. The cartridge may include a reservoir configured to contain an aerosol precursor composition. The cartridge may further include a valve assembly configured to dispense the aerosol precursor composition to the atomizer body when the cartridge is engaged with the atomizer body. The valve assembly may include a dispensing seal and a reservoir seal. The control body may be configured to releasably engage the atomizer body and the atomizer body may be configured to releasably engage the cartridge. The atomizer may be configured to receive an electrical current from the control body and the aerosol precursor composition from the cartridge to produce an aerosol.

In some embodiments the cartridge may include one or more air flow apertures extending from the atomizer body to a mouthpiece. The air flow apertures may be configured to direct the aerosol therethrough. At least one of the air flow apertures may extend through the valve assembly. The valve assembly may define a dispensing capillary tube and may further include a first plate and a second plate positioned adjacent to one another with a space defined therebetween. The dispensing capillary tube may extend through the first plate to the space between the first plate and the second plate. A gap may be defined between a radial outer edge of the first plate and a radial outer edge of the second plate and an inner surface of the reservoir.

In some embodiments the atomizer body may further include a nozzle configured to extend through the reservoir seal and engage the dispensing seal. The valve assembly may further include a frame and the reservoir seal may be molded to the frame. The atomizer may include a liquid transport element that may include a porous monolith. The atomizer may further include a heating element that may include a wire at least partially imbedded in the liquid transport element. The liquid transport element may define a tube and the atomizer may further include a capillary rod extending through the liquid transport element and configured to direct the aerosol precursor composition therethrough. The control body may further include a microphone. The microphone may be configured to detect a user draw on the cartridge.

In some embodiments, the atomizer may comprise an outer body, a terminal base, a flow director, and a liquid transport element comprising a porous monolith, and an atomizer chamber may be created by the flow director, the terminal base, and an inside surface of the liquid transport element. The flow director may include a central inlet air channel, a transition barrier, and one or more radial inlet air holes configured such that air that enters through the inlet air channel may be directed through the one or more radial inlet air holes by the transition barrier. The flow director may further include one or more inlet liquid flow chambers configured to deliver the aerosol precursor composition to the liquid transport element. The outer body may include one or more vapor apertures, and the flow director may further include one or more radial inlet vapor holes, one or more radial vapor channels, and one or more vertical vapor holes, configured such that the aerosol may be directed through the one or more radial inlet vapor holes, the one or more radial vapor channels, the one or more vertical vapor holes of the flow director, and the one or more vapor apertures of the outer body and into one or more vapor channels of the cartridge.

In an additional aspect, an aerosol delivery device operation method is provided. The aerosol delivery device operation method may include directing an aerosol precursor composition from a reservoir of a cartridge out of the cartridge through a valve assembly by directing the aerosol precursor composition through a dispensing seal and a reservoir seal at the reservoir. The method may further include receiving the aerosol precursor composition in an atomizer body. Additionally, the method may include directing the aerosol precursor composition to an atomizer in the atomizer body. Further, the method may include directing an electrical current from a control body to the atomizer to produce an aerosol.

In some embodiments the valve assembly may define a dispensing capillary tube and directing the aerosol precursor composition out of the cartridge through the valve assembly may further include directing the aerosol precursor composition between a first plate and a second plate positioned adjacent to one another with a space defined therebetween and out of the space through the dispensing capillary tube extending through the first plate. Directing the aerosol precursor composition out of the cartridge through the valve assembly may further include engaging a nozzle of the atomizer body with the valve assembly. Engaging the nozzle with the valve assembly may include directing the nozzle through the reservoir seal of the valve assembly. Engaging the nozzle with the valve assembly may further include engaging the nozzle with the dispensing seal of the valve assembly at the dispensing capillary tube.

In some embodiments receiving the aerosol precursor composition in the atomizer body may include directing the aerosol precursor composition between the nozzle and a capillary rod. Directing the aerosol precursor composition to the atomizer in the atomizer body may include directing the aerosol precursor composition between the capillary rod and a liquid transport element of the atomizer. The method may further include directing the aerosol through one or more air flow apertures extending through the cartridge. Directing the aerosol through one or more air flow apertures extending through the cartridge may include directing the aerosol through the valve assembly.

In some embodiments, directing the aerosol precursor composition to an atomizer in the atomizer body may comprise directing the aerosol precursor composition through one or more radial flow openings in an outer body of the atomizer and through one or more inlet liquid flow channel in a flow director of the atomizer. Some embodiments may further comprise directing the aerosol through one or more radial inlet vapor holes, one or more radial vapor channels, and one or more vertical vapor holes of the flow director, one or more vapor apertures of an outer body of the atomizer, and into one or more vapor channels of the cartridge.

These and other features, aspects, and advantages of the disclosure will be apparent from a reading of the following detailed description together with the accompanying drawings, which are briefly described below.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
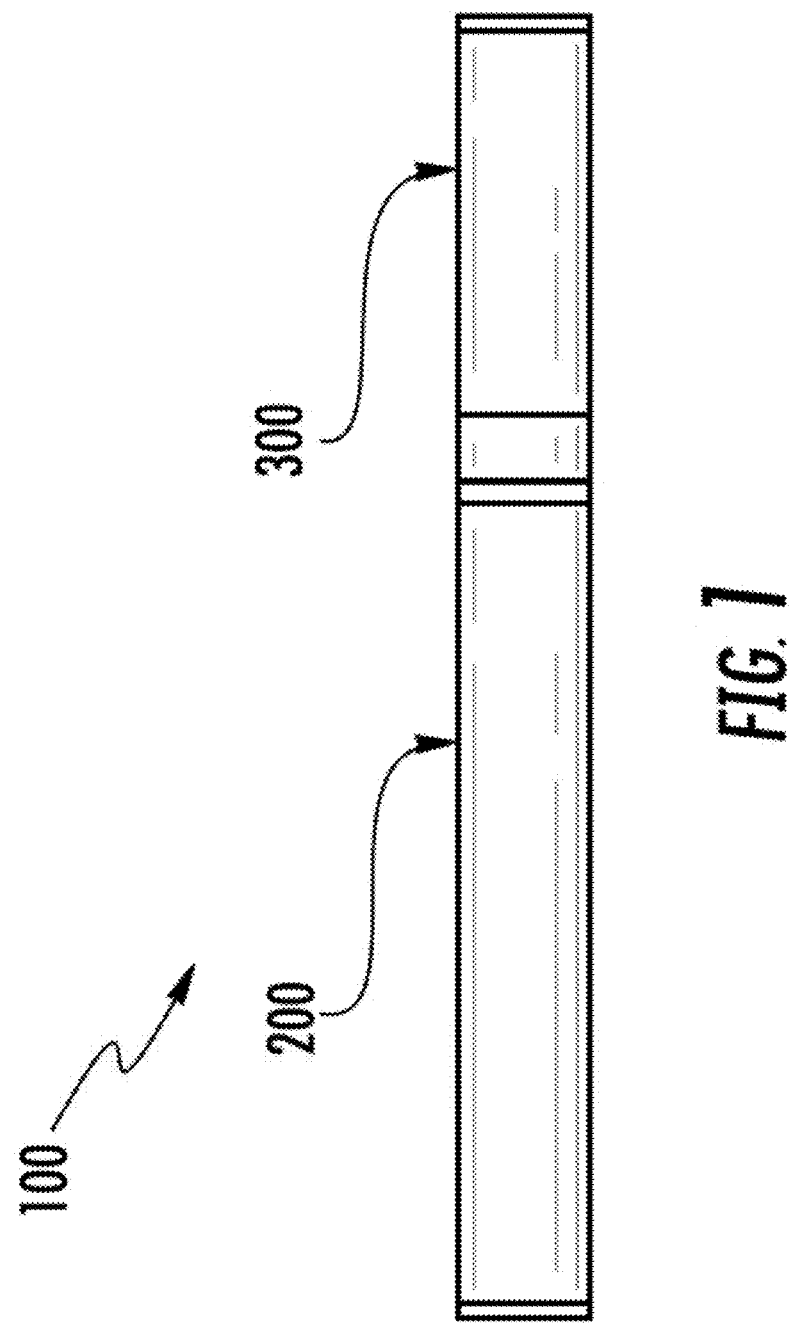
Figure 2:
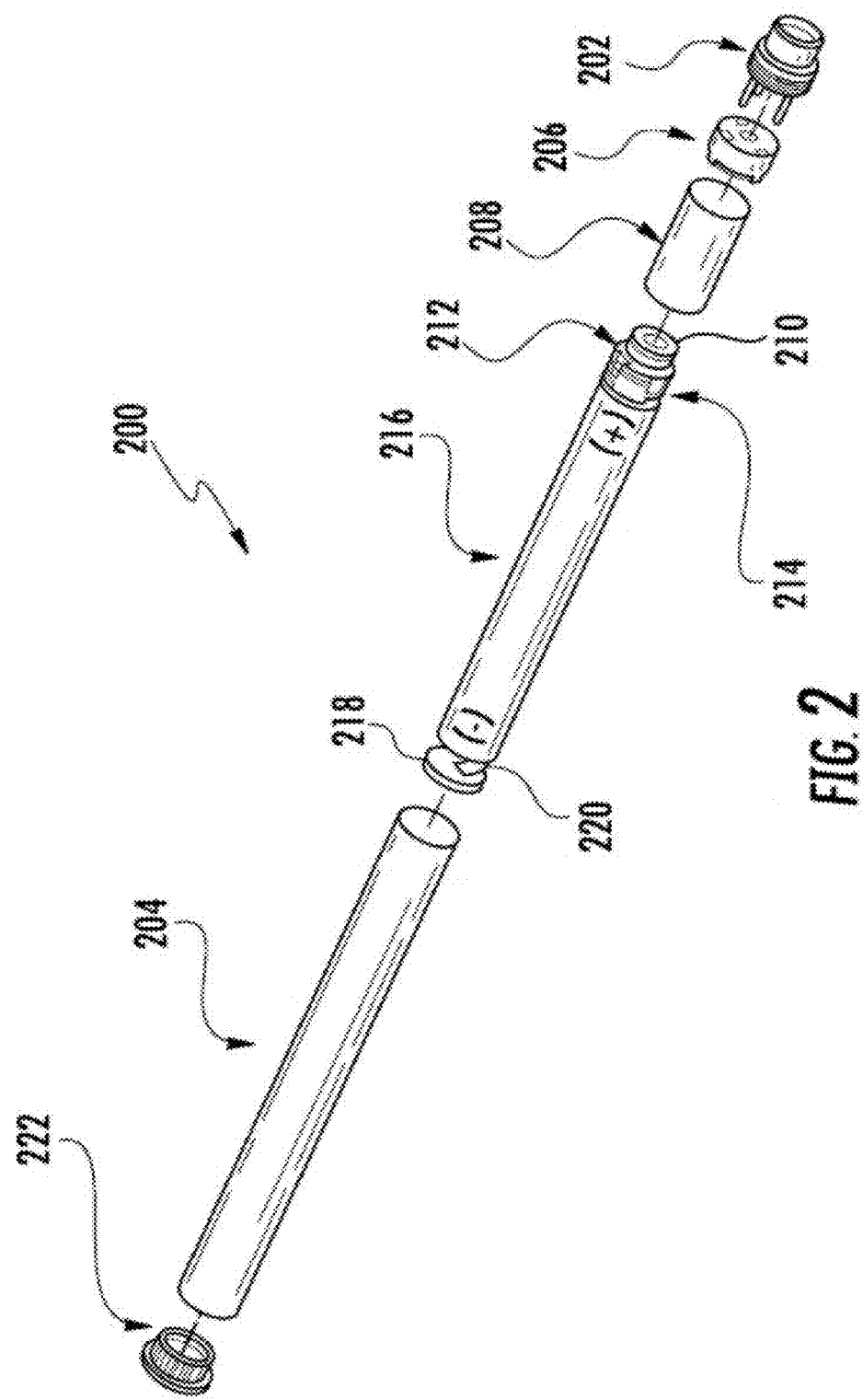
Figure 3:
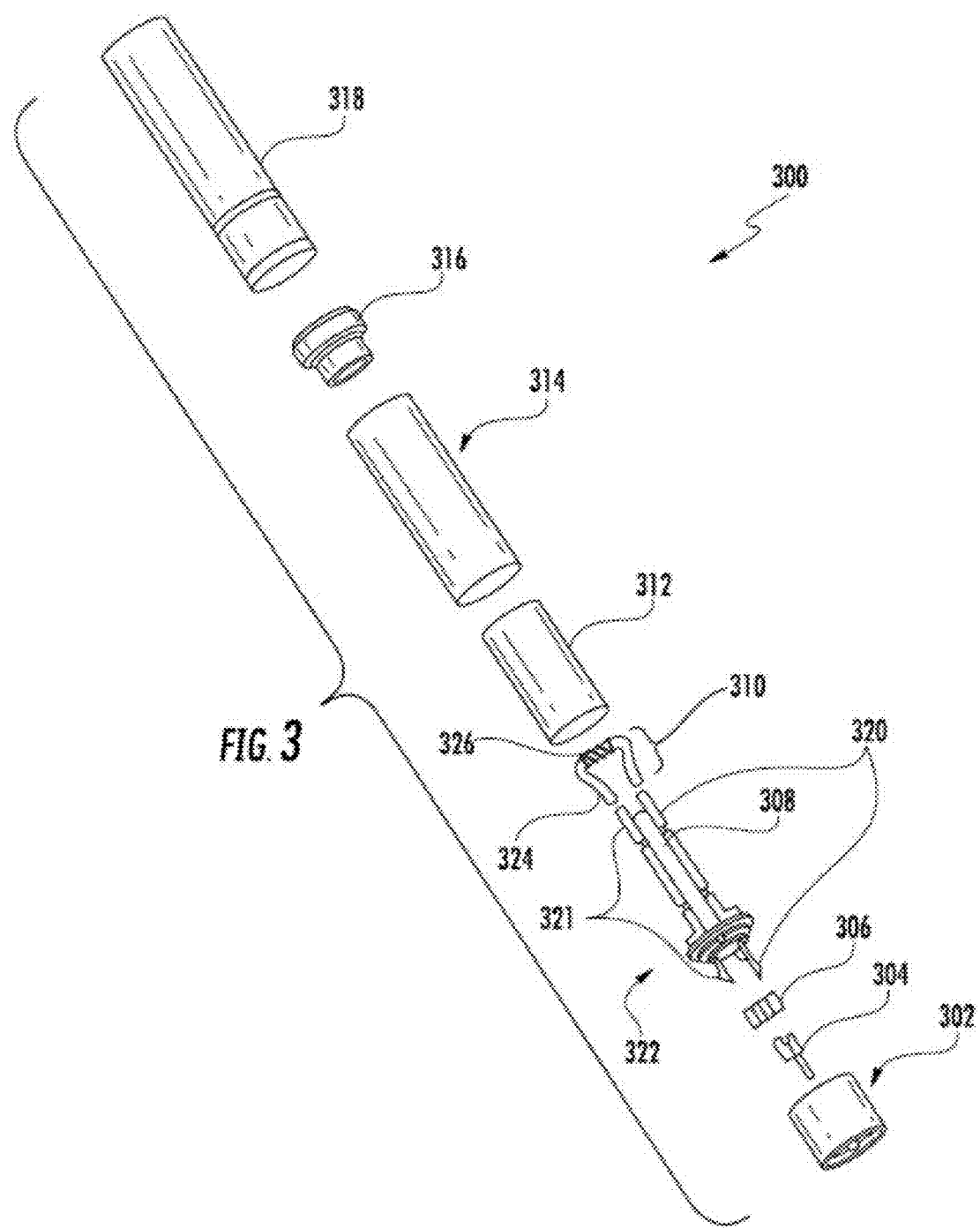
Figure 4:
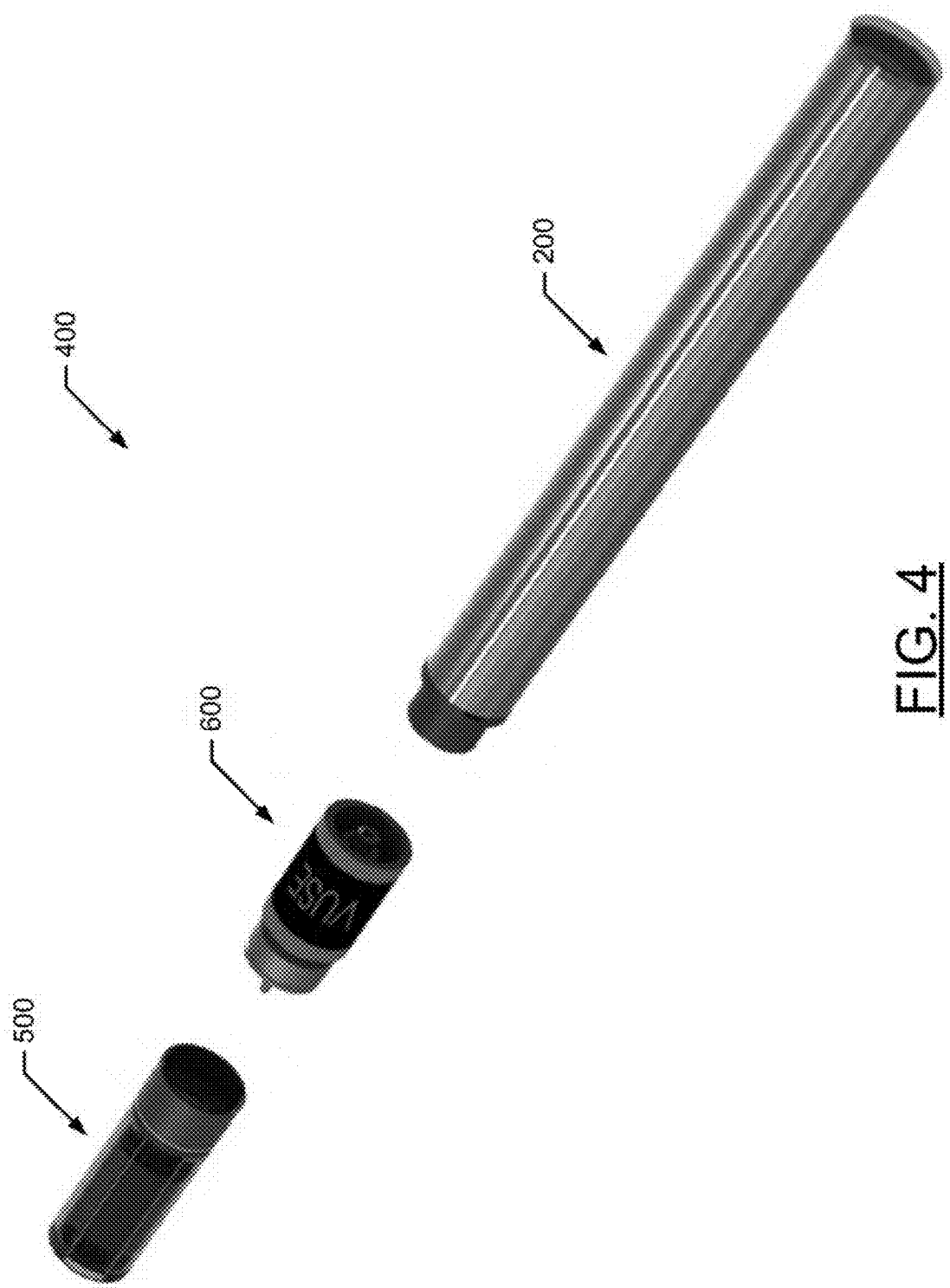
Figure 5:
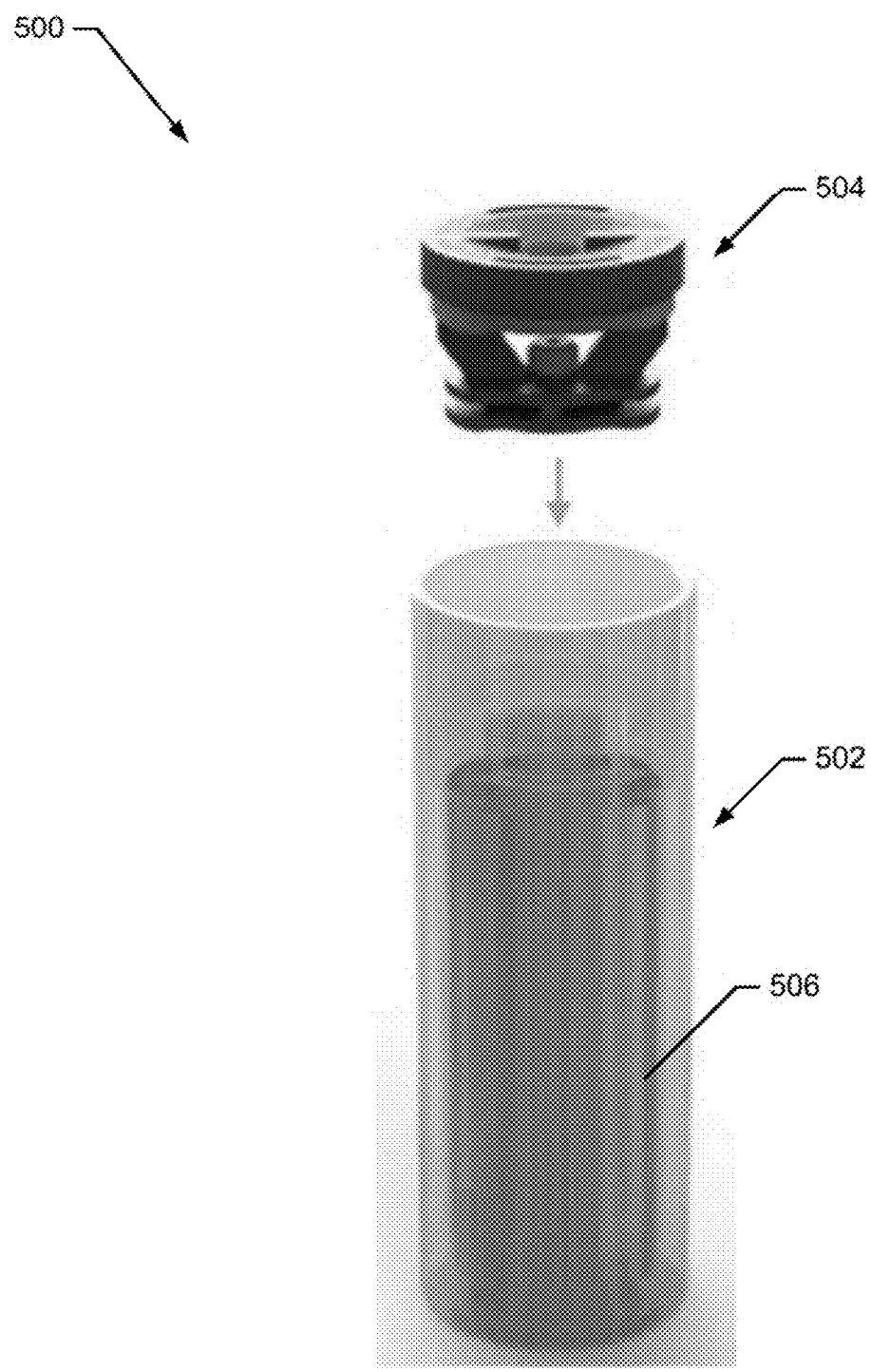
Figure 6:
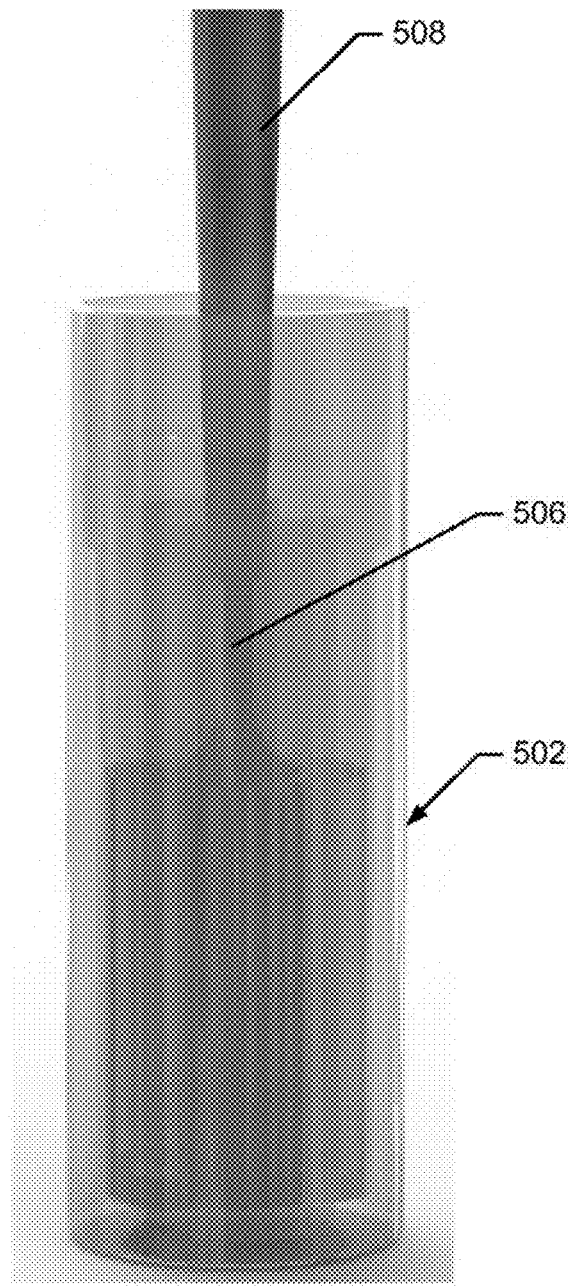
Figure 7:
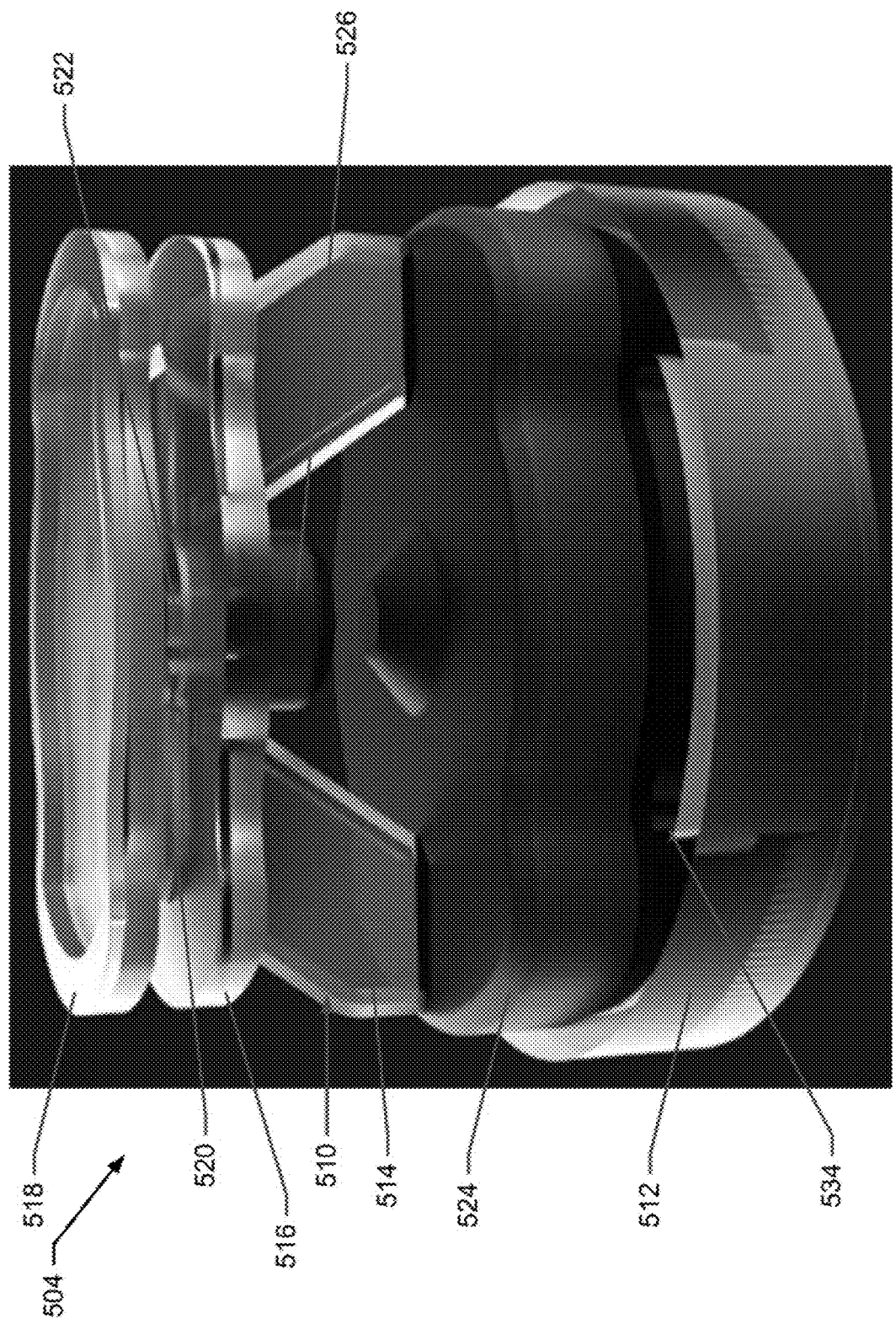
Figure 8:
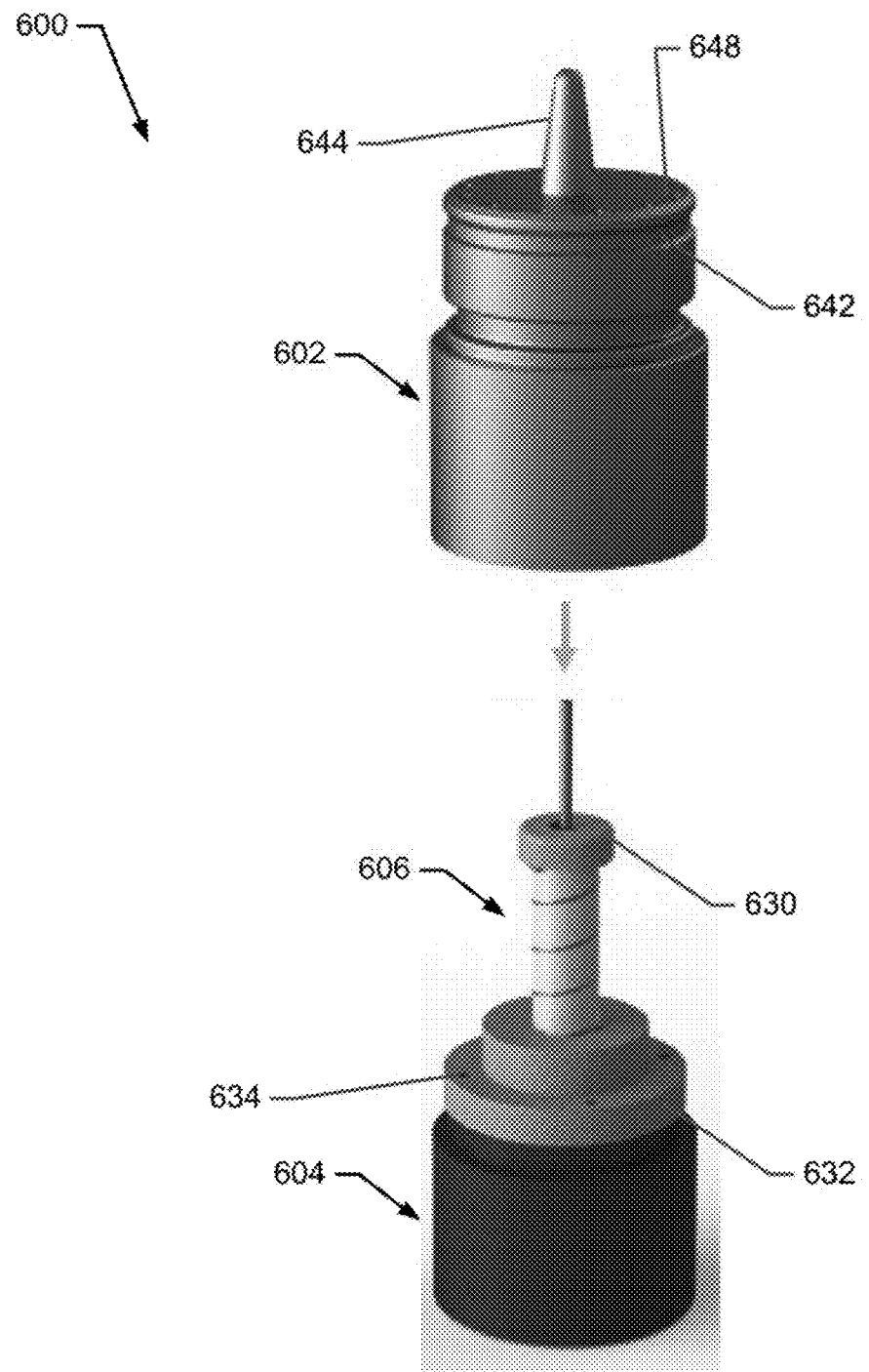
Figure 9:
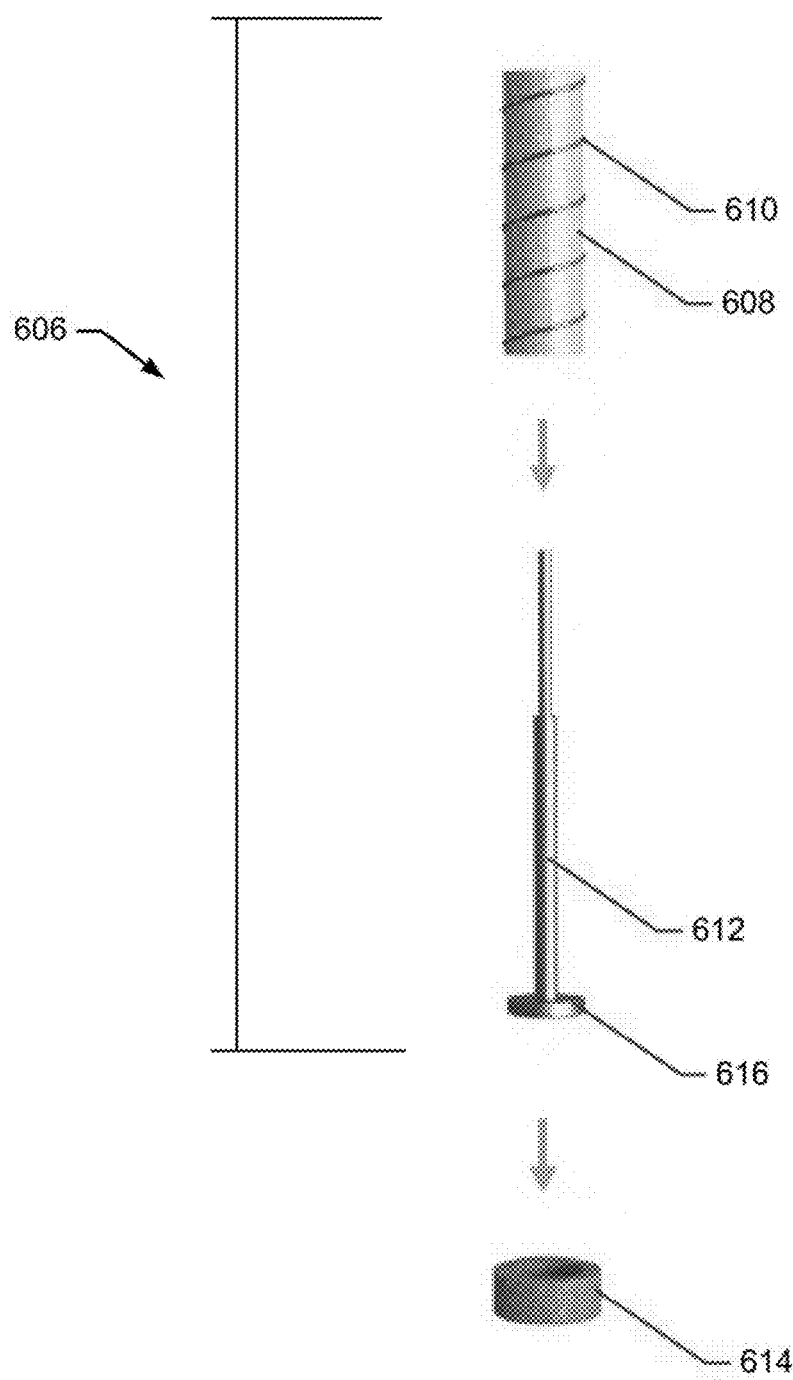
Figure 10:
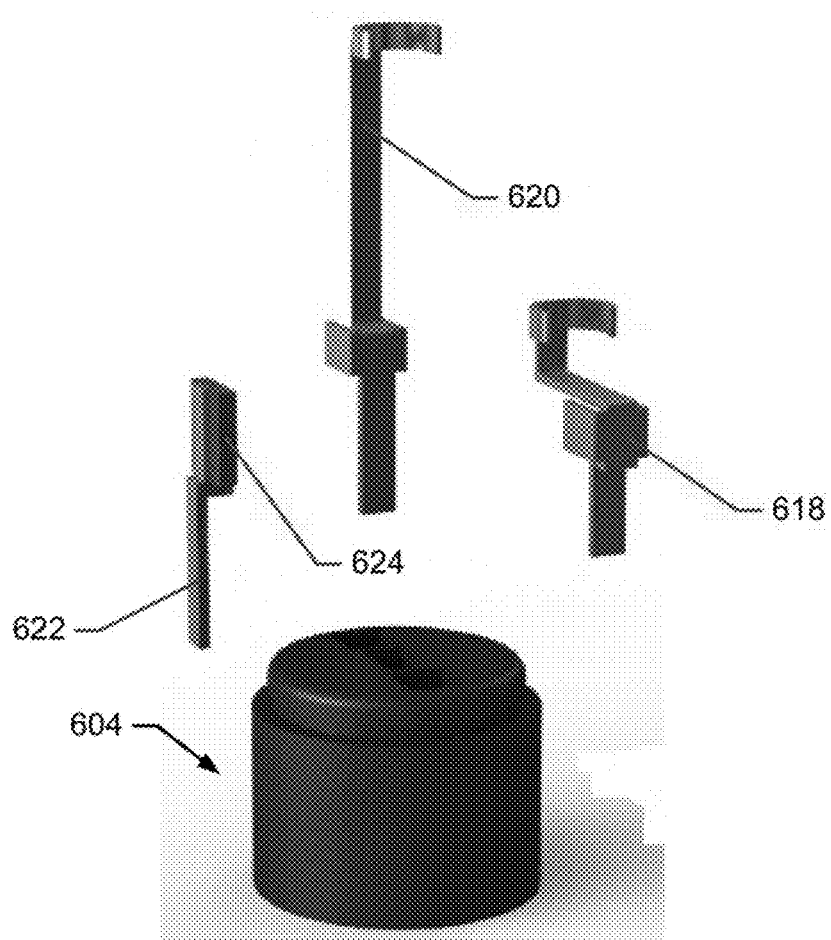
Figure 11:
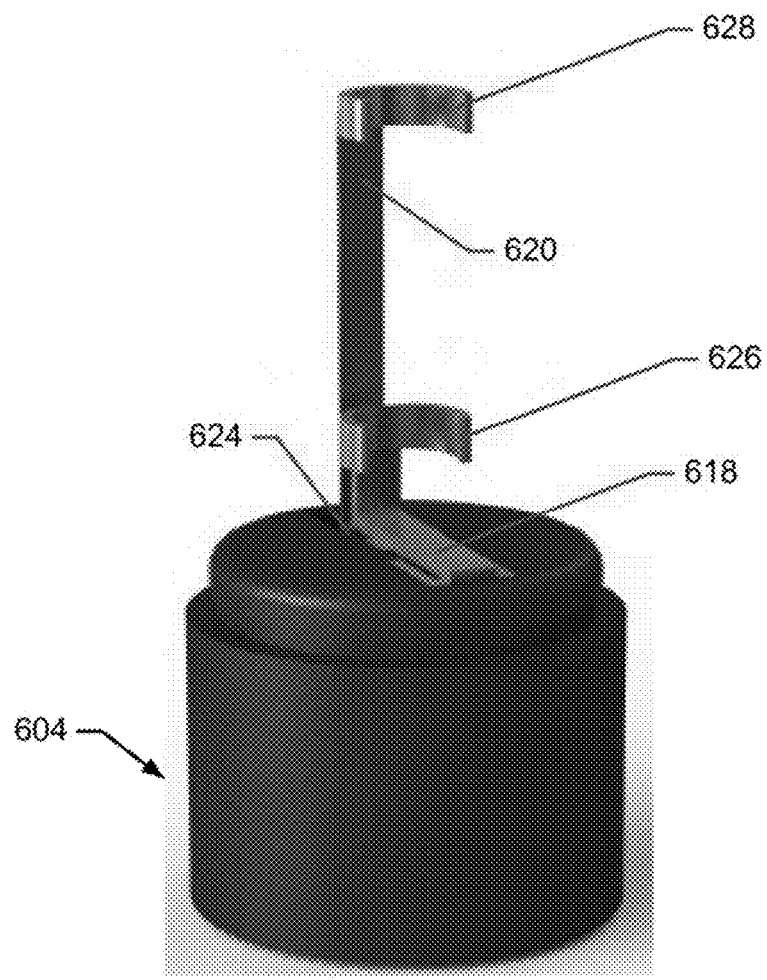
Figure 12:
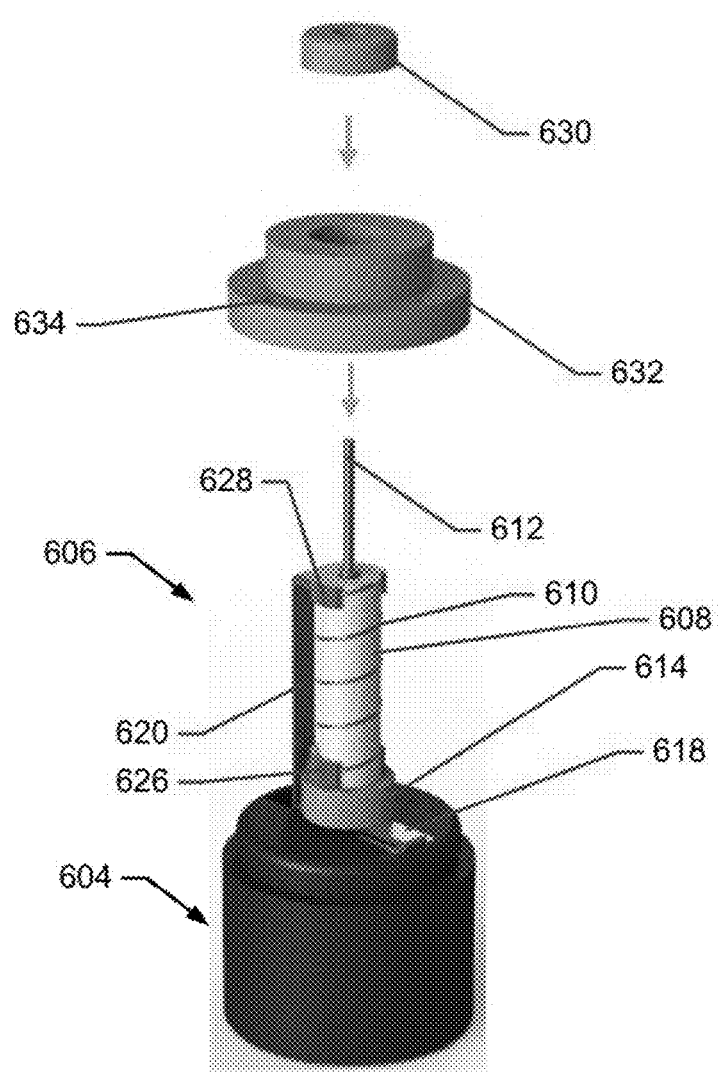
Figure 13:
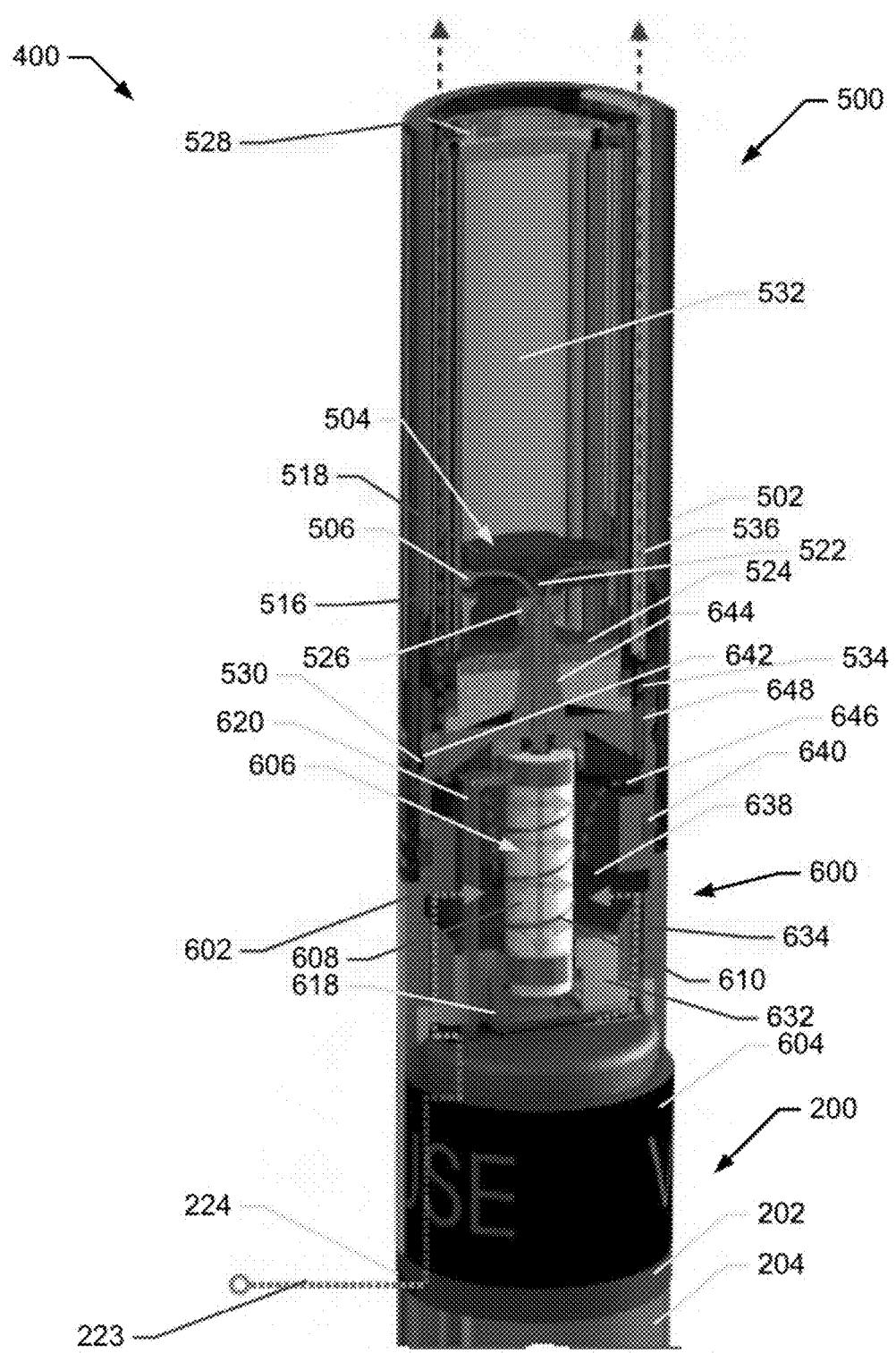
Figure 14:
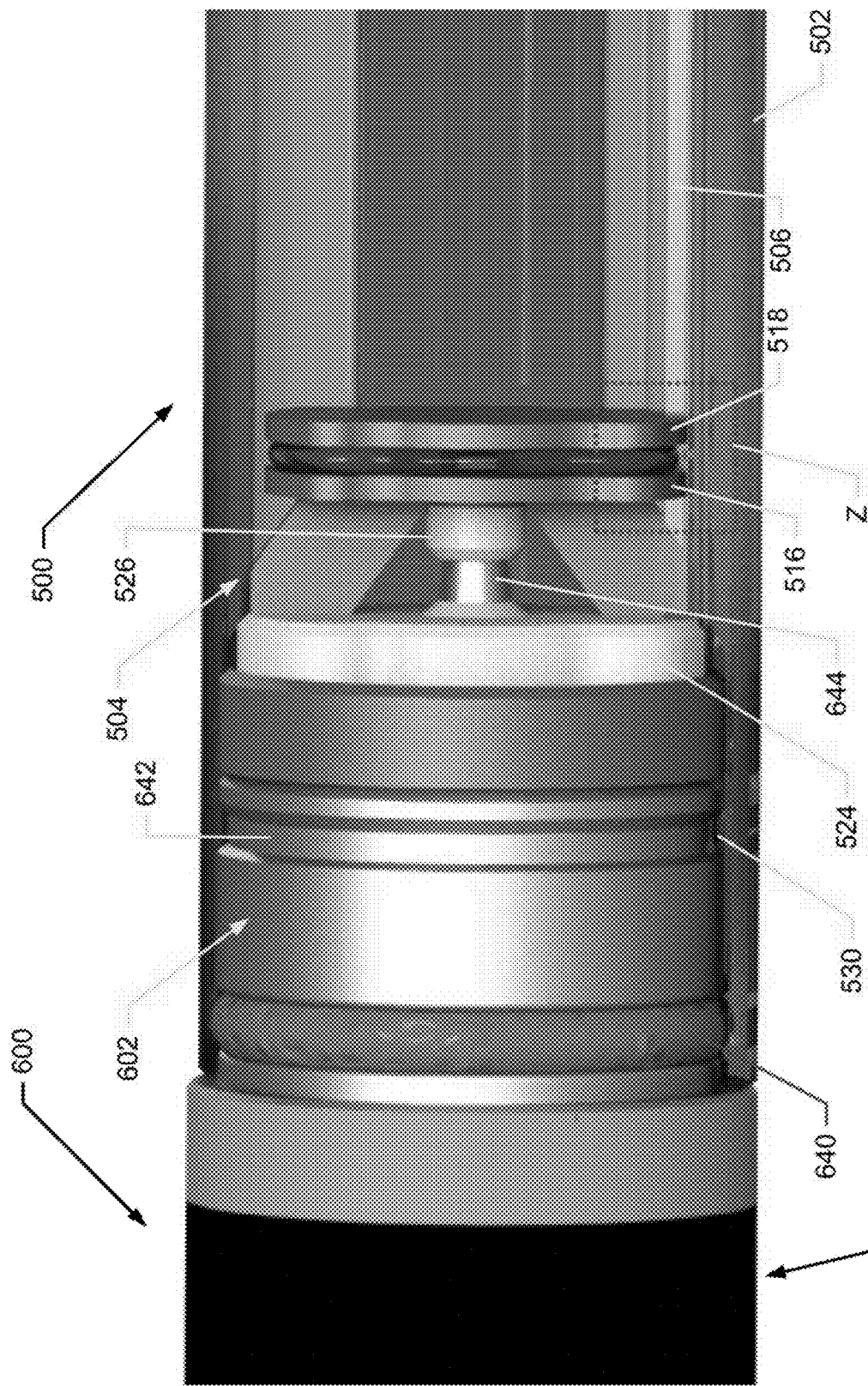
Figure 15:
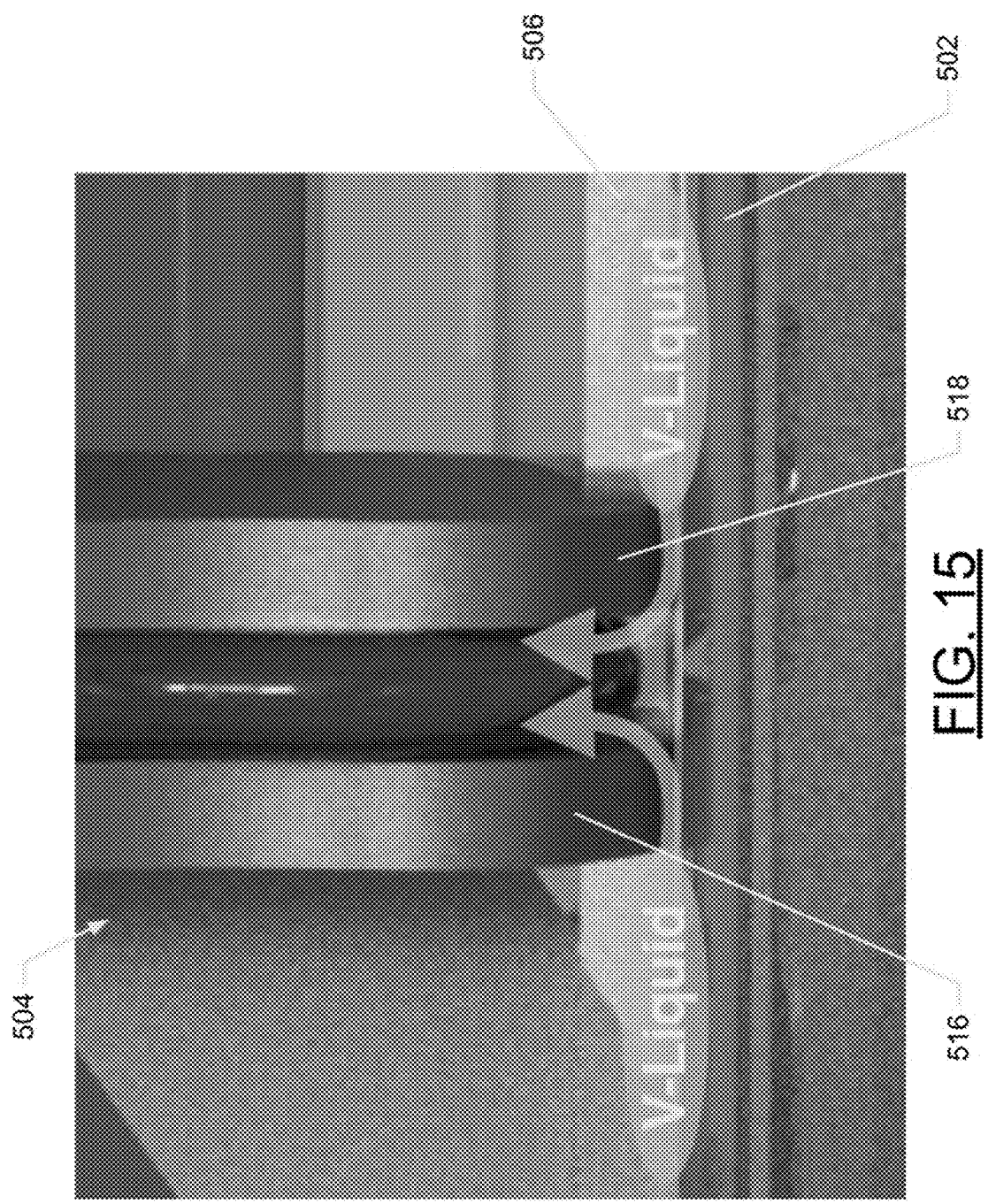
Figure 16:
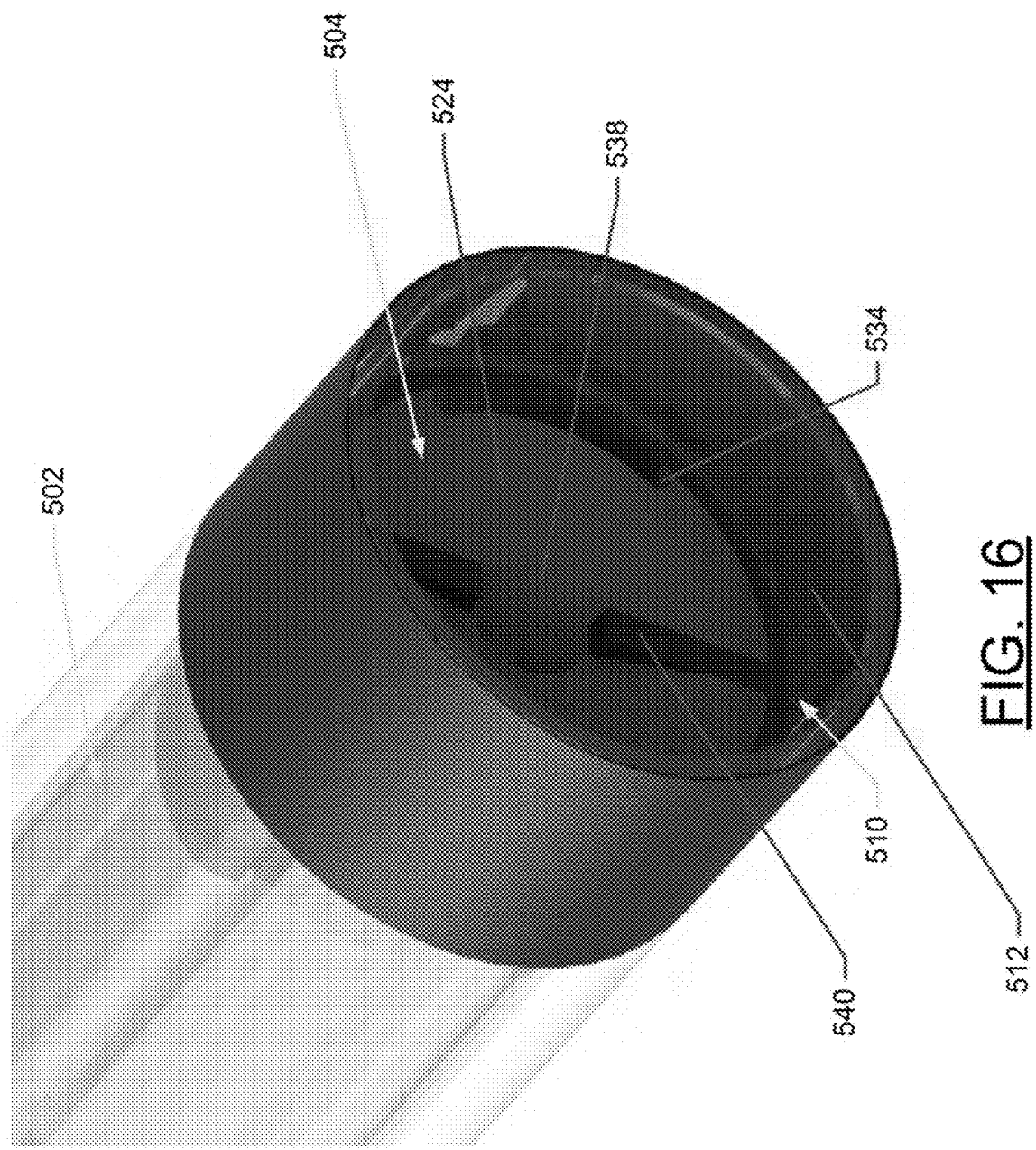
Figure 18:
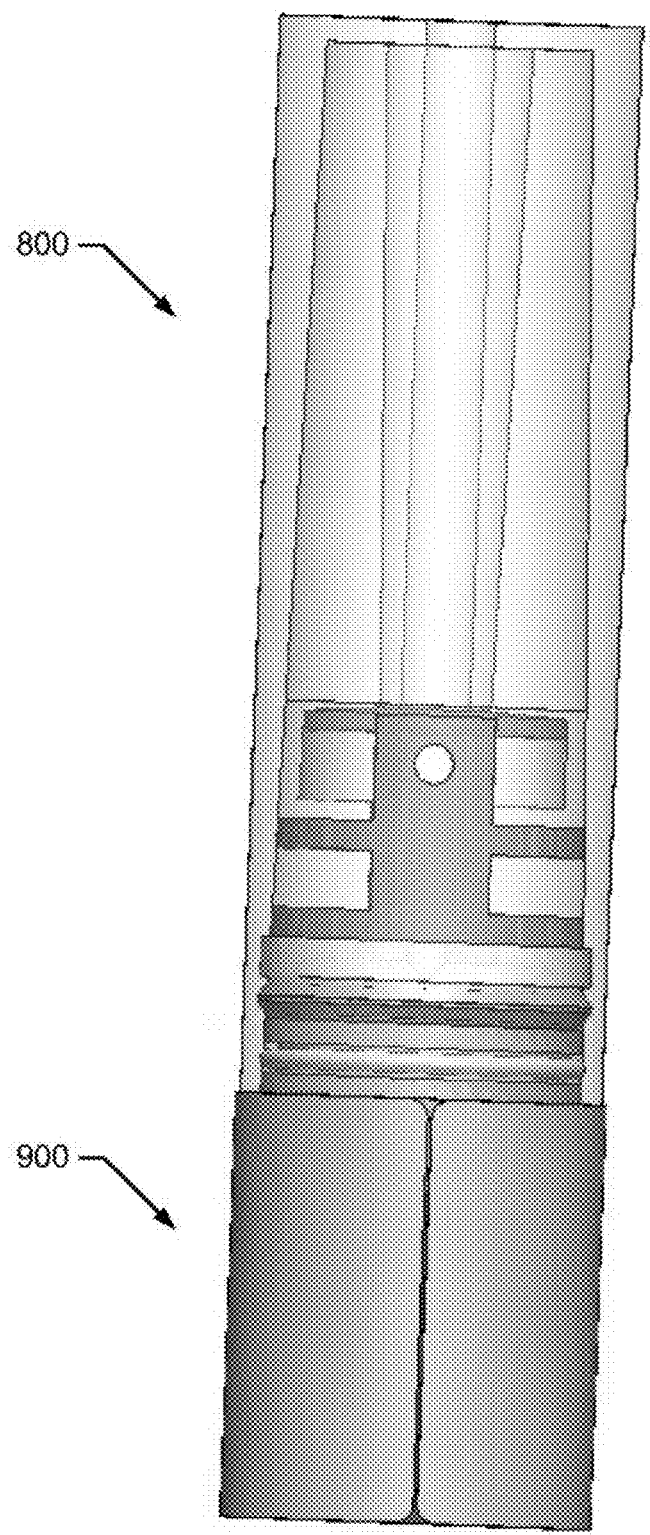
Figure 19:
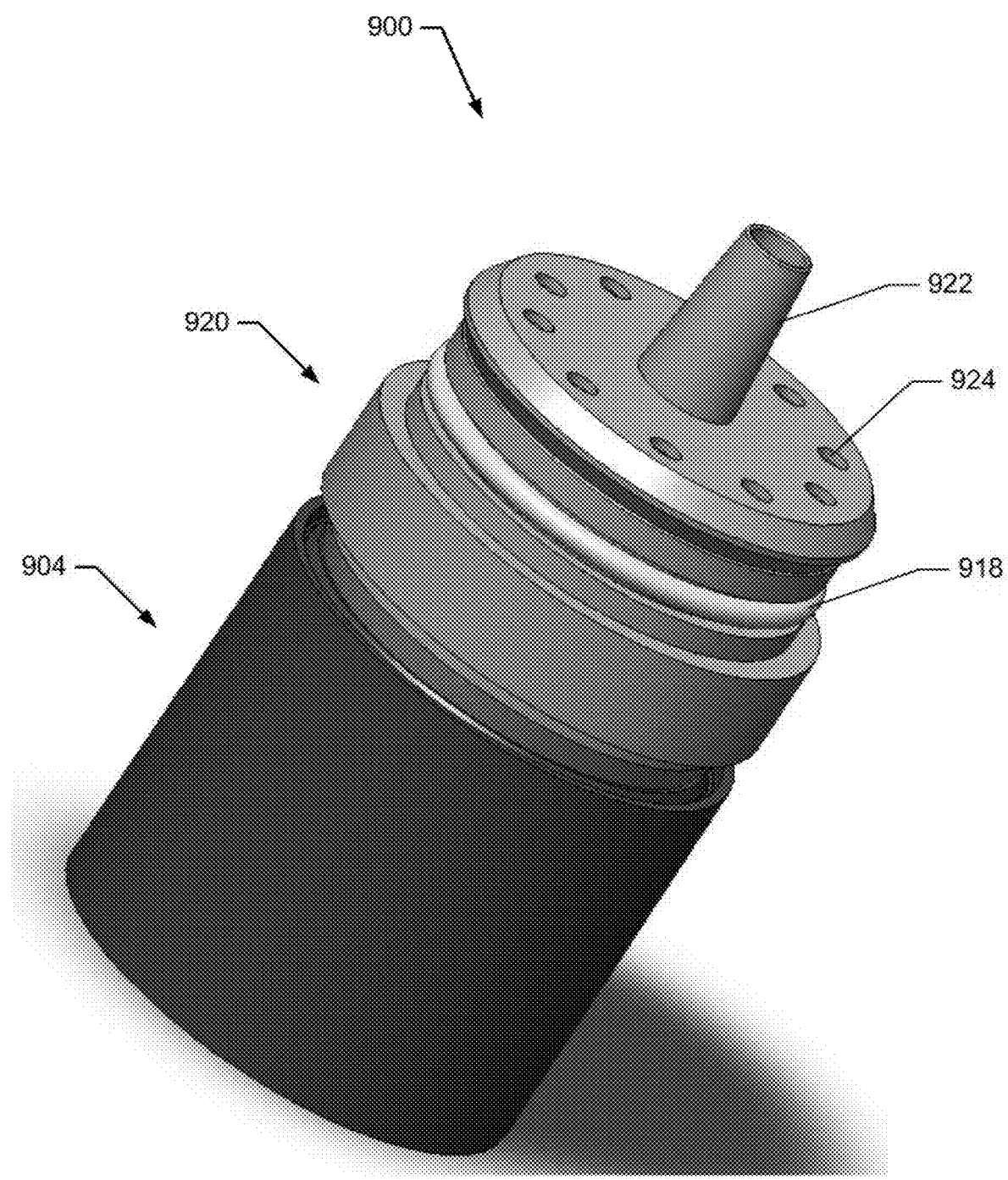
Figure 20:
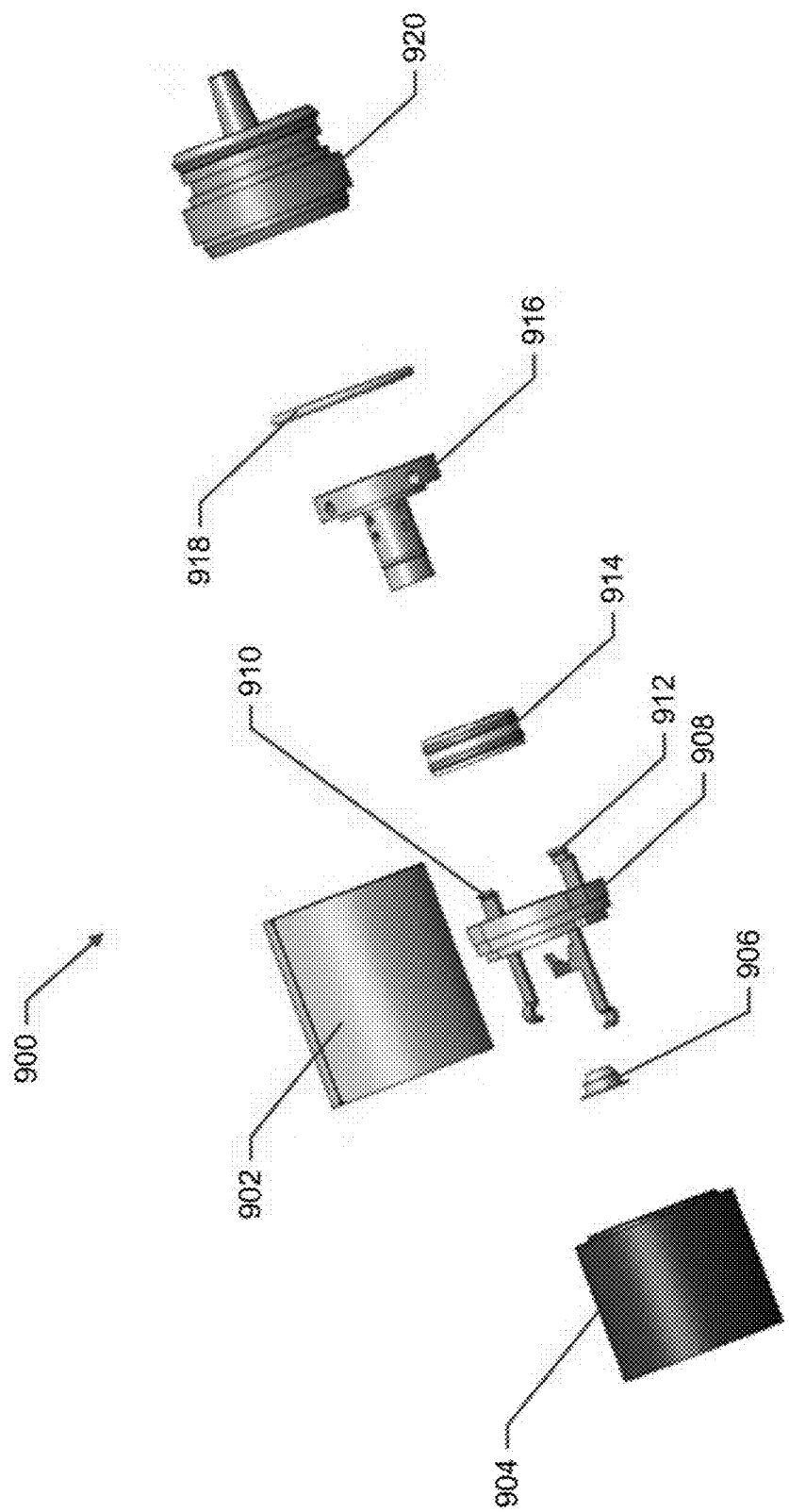
Figure 21:
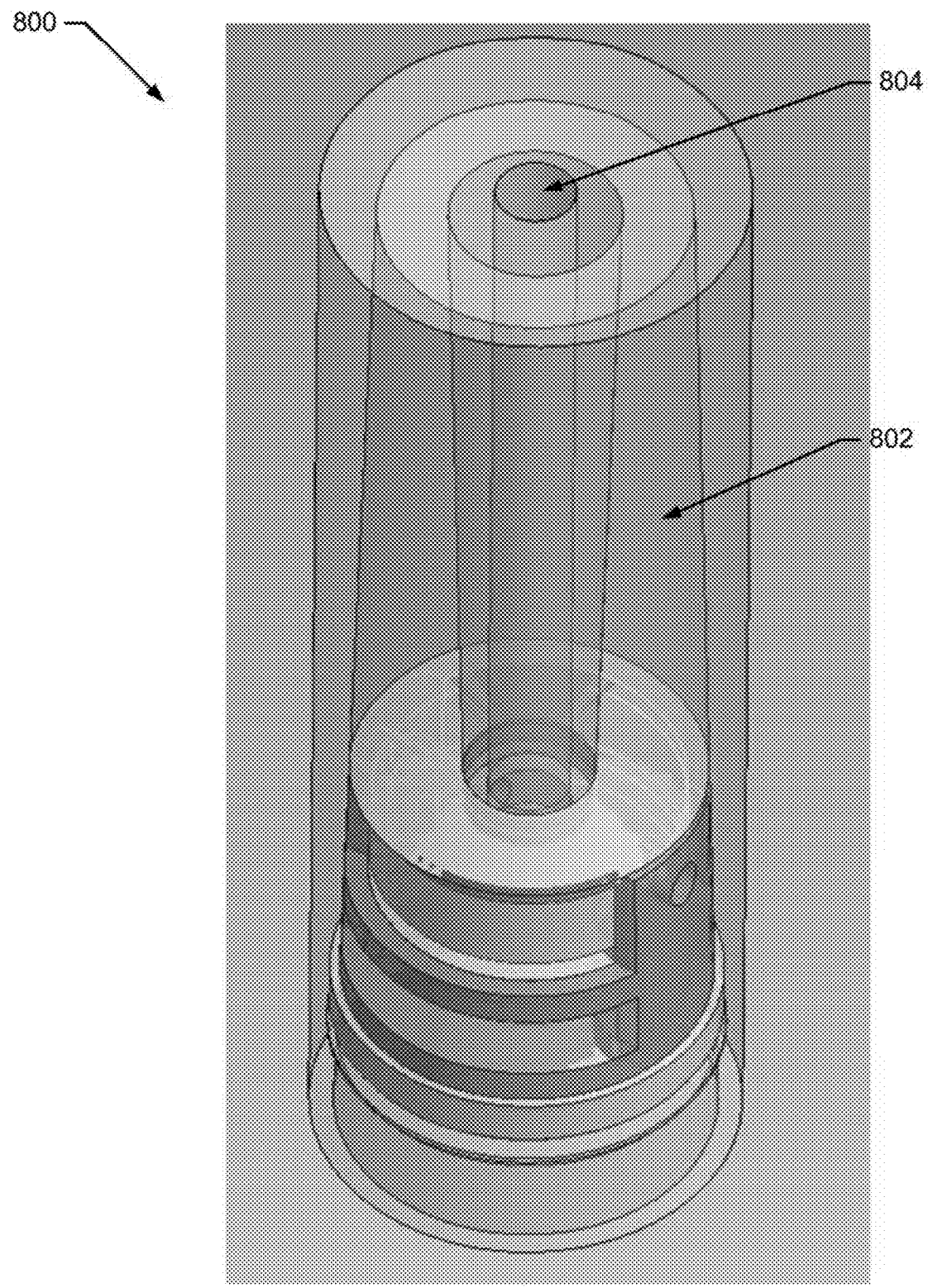
Figure 22:
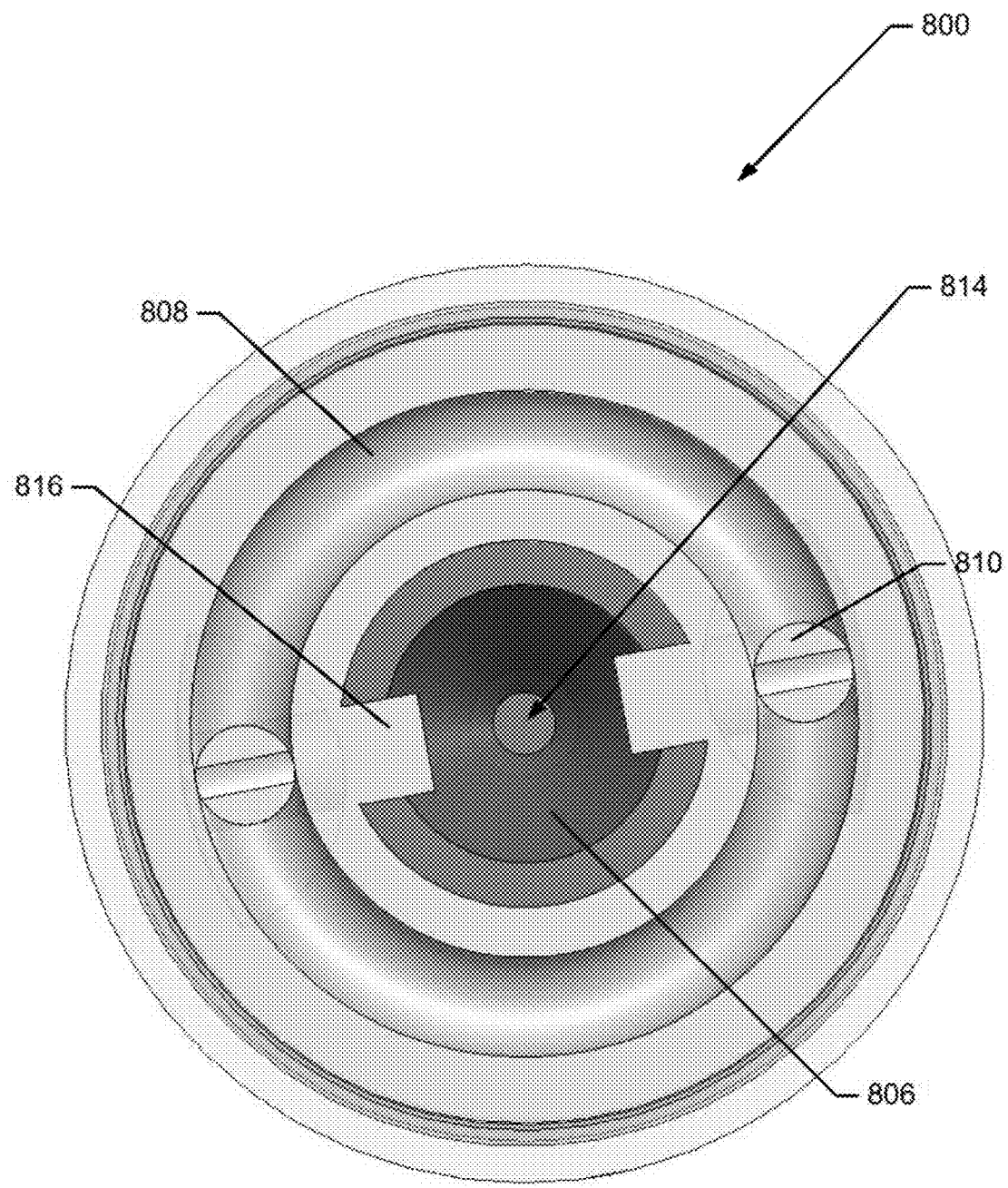
Figure 23:
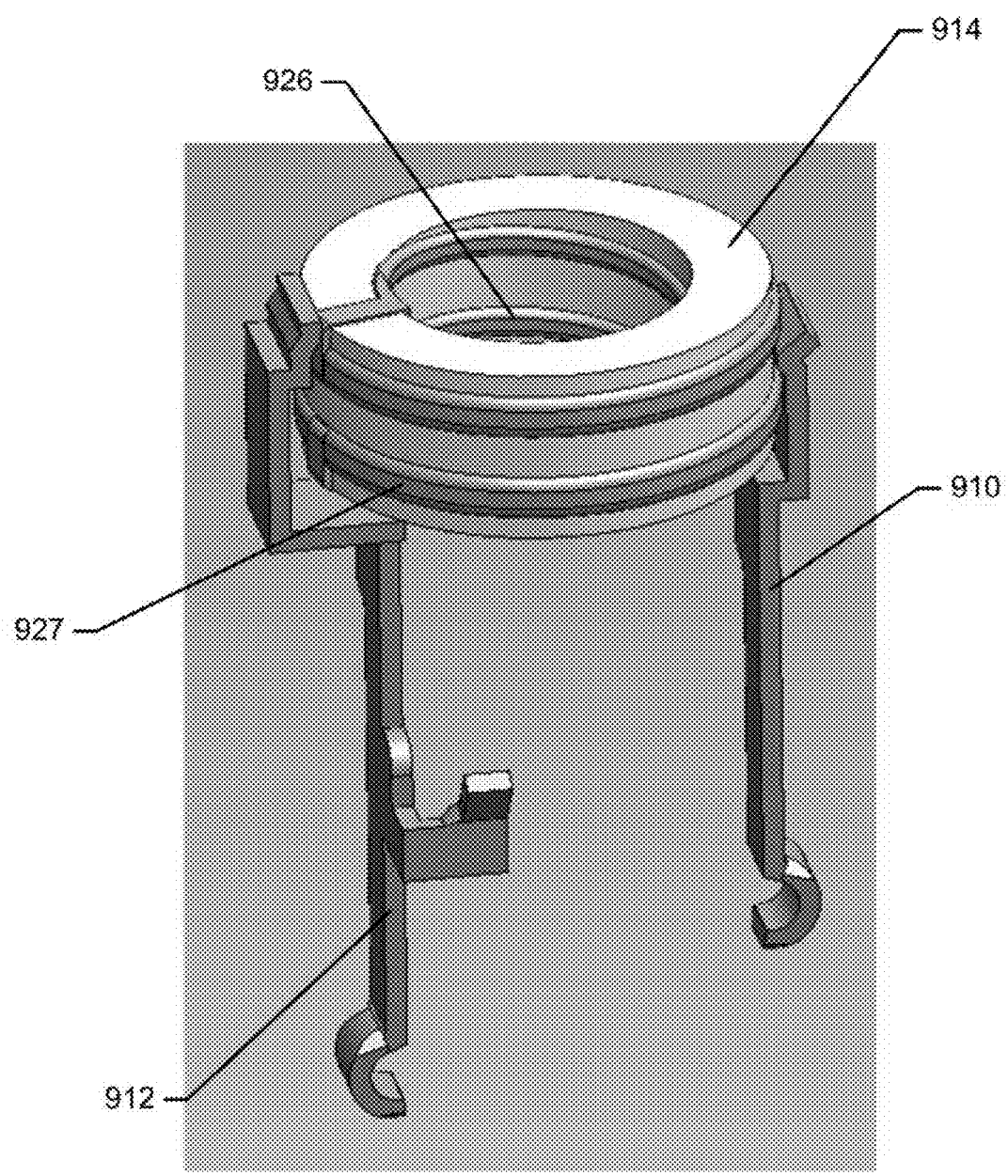
Figure 24:
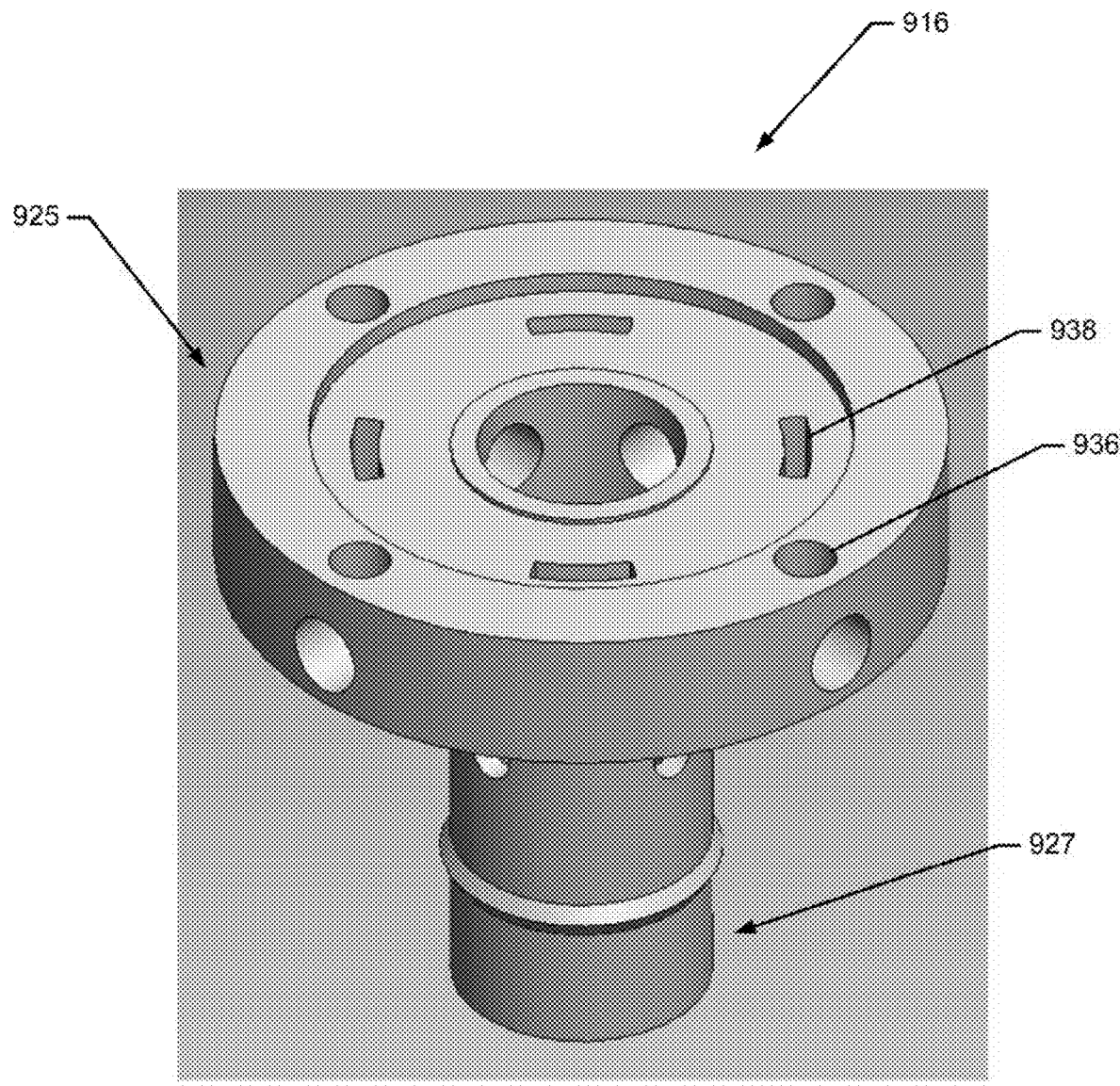
Figure 25:
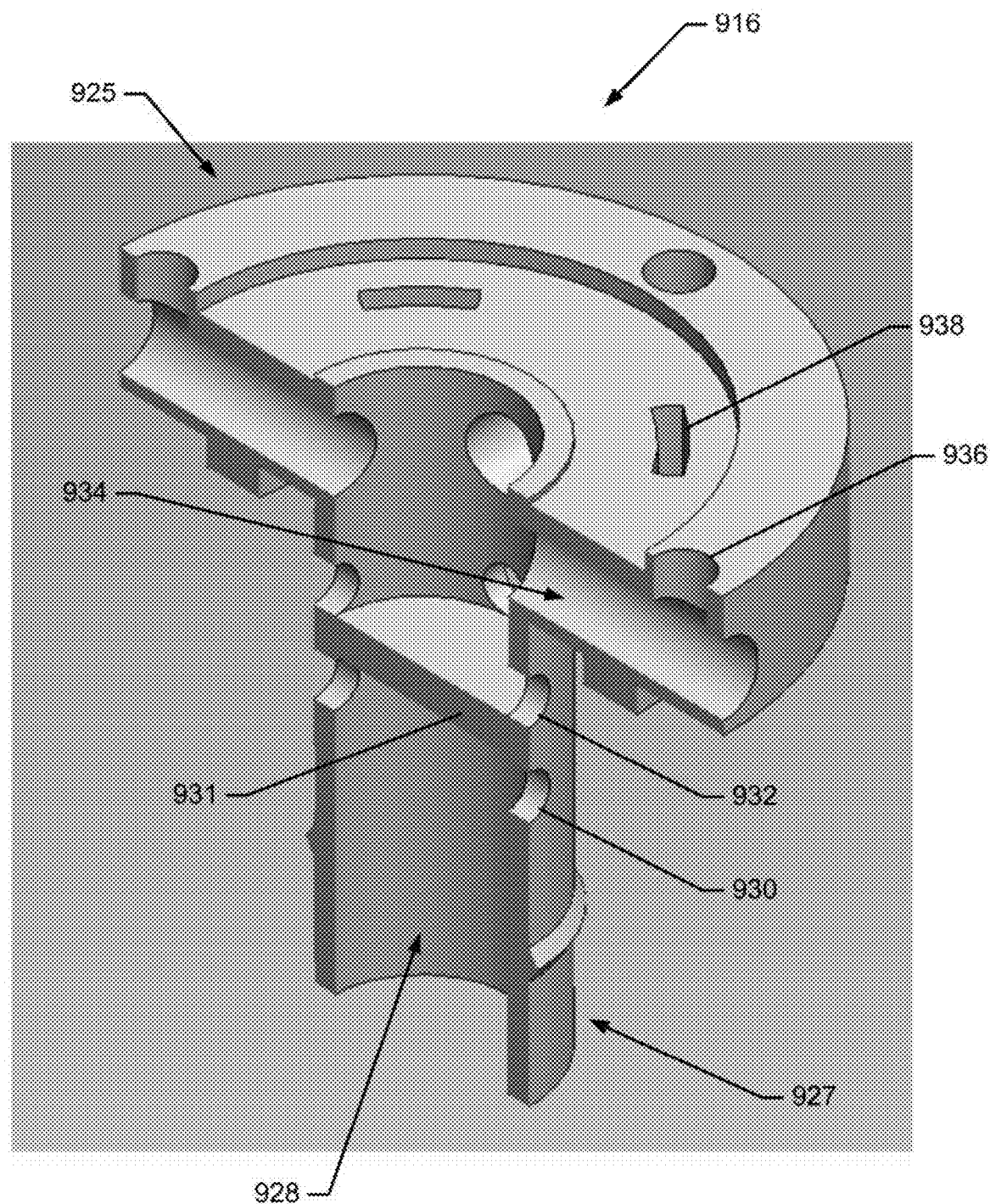
Figure 26:
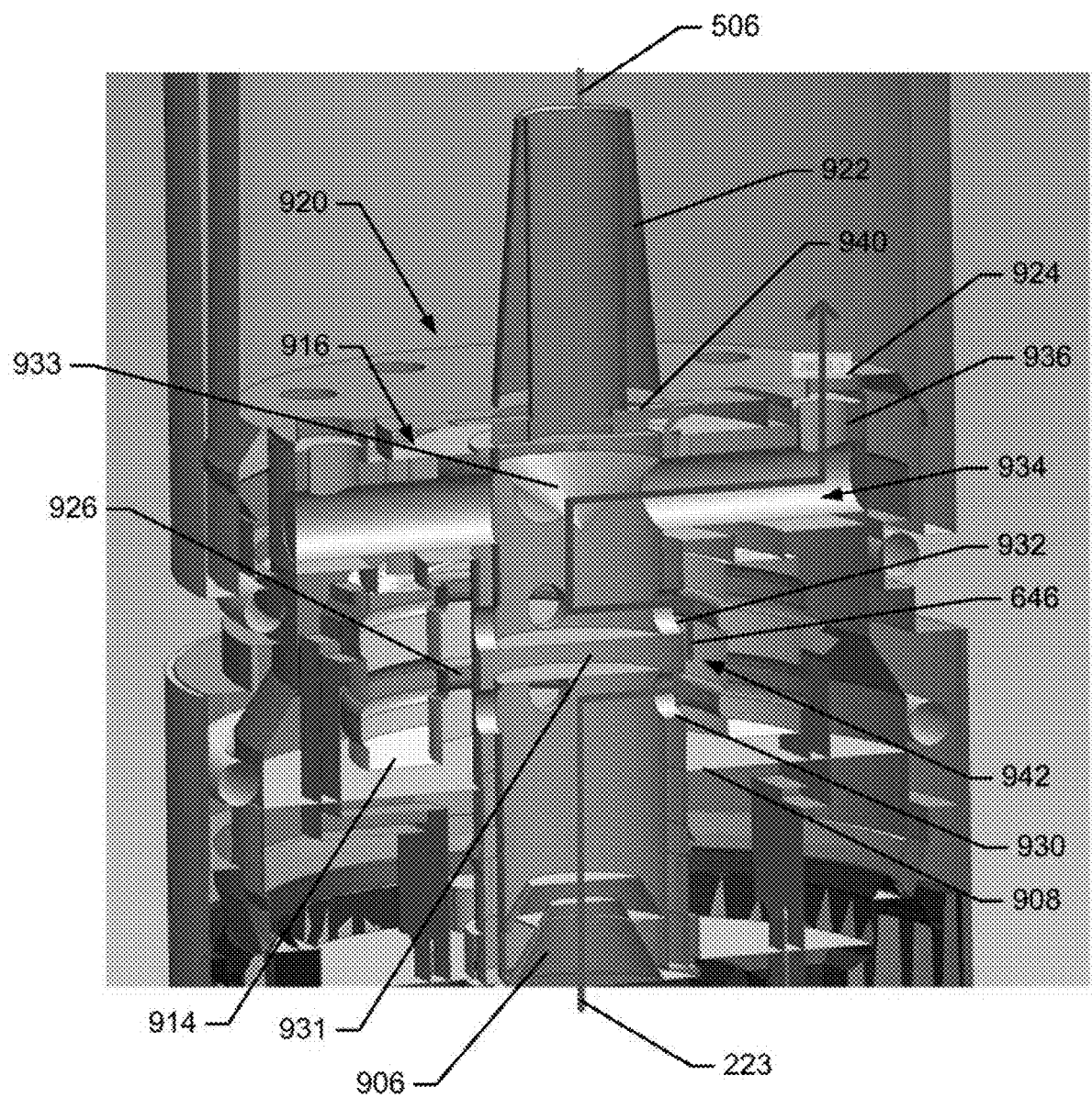
Figure 27:
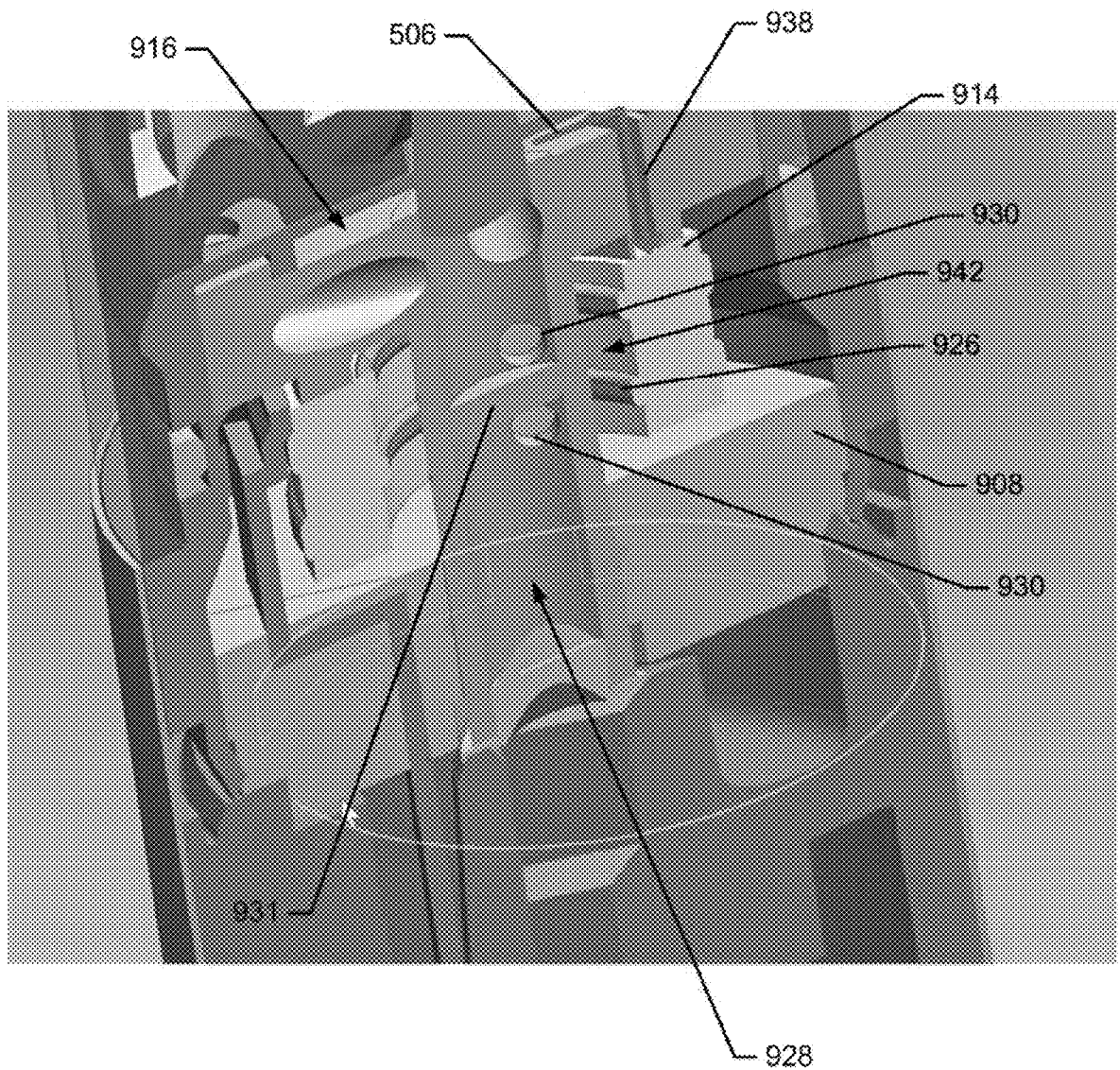
Figure 28:
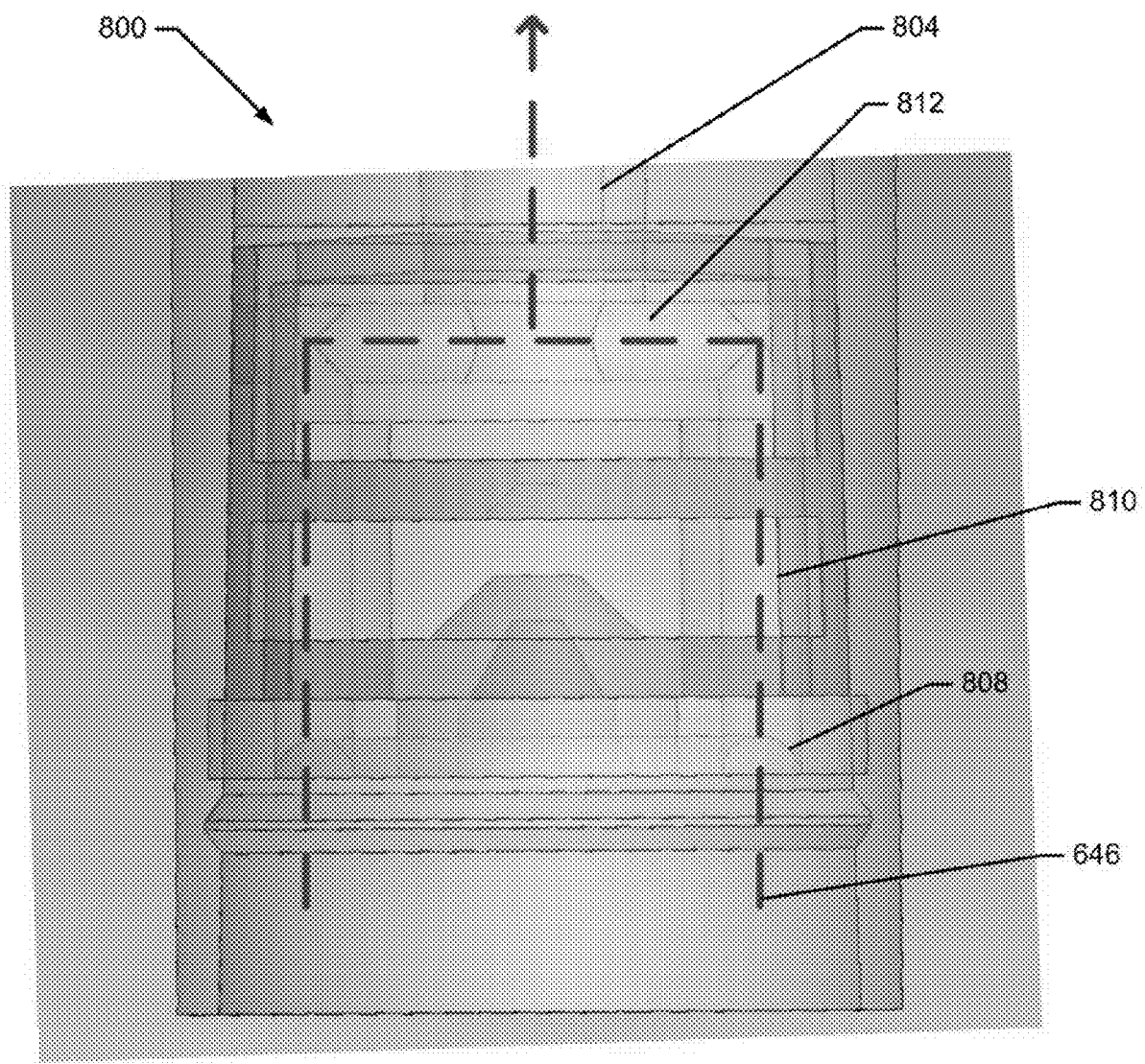

Having thus described the disclosure in the foregoing general terms, reference will now be made to the accompanying drawings, which are not necessarily drawn to scale, and wherein:

FIG. 1 illustrates a side view of an aerosol delivery device comprising a cartridge and a control body in an assembled configuration according to an example embodiment of the present disclosure;

FIG. 2 illustrates the control body of FIG. 1 in an exploded configuration according to an example embodiment of the present disclosure;

FIG. 3 illustrates the cartridge of FIG. 1 in an exploded configuration according to an example embodiment of the present disclosure;

FIG. 4 illustrates a perspective view of an aerosol delivery device including a cartridge, an atomizer body, and a control body in a decoupled configuration according to an example embodiment of the present disclosure;

FIG. 5 illustrates an exploded view of the cartridge of FIG. 4 including a reservoir and a valve assembly according to an example embodiment of the present disclosure;

FIG. 6 illustrates a perspective view of filling of the reservoir of FIG. 5 according to an example embodiment of the present disclosure;

FIG. 7 illustrates a perspective view of the valve assembly of FIG. 5 according to an example embodiment of the present disclosure;

FIG. 8 illustrates an exploded view of the atomizer body of FIG. 4 including an outer body, an atomizer, and a coupler according to an example embodiment of the present disclosure;

FIG. 9 illustrates an exploded view of the atomizer of FIG. 8 according to an example embodiment of the present disclosure;

FIG. 10 illustrates an exploded view of the coupler and terminals of the atomizer body of FIG. 4 according to an example embodiment of the present disclosure;

FIG. 11 illustrates a perspective view of the coupler and the terminals of FIG. 10 in an assembled configuration according to an example embodiment of the present disclosure;

FIG. 12 illustrates a partially assembled, partially exploded view of part of the atomizer body of FIG. 4 according to an example embodiment of the present disclosure;

FIG. 13 illustrates a modified sectional view through the aerosol delivery device of FIG. 4 according to an example embodiment of the present disclosure;

FIG. 14 illustrates a modified sectional view through the aerosol delivery device of FIG. 4 at the cartridge according to an example embodiment of the present disclosure;

FIG. 15 illustrates an enlarged view of area Z from FIG. 14 according to an example embodiment of the present disclosure;

FIG. 16 illustrates a perspective end view of the cartridge of FIG. 4 according to an example embodiment of the present disclosure;

FIG. 17 schematically illustrates an aerosol delivery device operation method according to an example embodiment of the present disclosure;

FIG. 18 illustrates a cartridge and an atomizer according to an additional example embodiment of the present disclosure;

FIG. 19 illustrates the atomizer of FIG. 18 in an assembled configuration according to an example embodiment of the present disclosure;

FIG. 20 illustrates the atomizer of FIG. 18 an exploded configuration according to an example embodiment of the present disclosure;

FIG. 21 illustrates a cartridge for use with the atomizer of FIG. 18 according to an example embodiment of the present disclosure;

FIG. 22 illustrates a bottom view of the cartridge of FIG. 21 according to an example embodiment of the present disclosure;

FIG. 23 illustrates a liquid transport element and a heating element for use with the atomizer of FIG. 18 according to an example embodiment of the present disclosure;

FIG. 24 illustrates a flow director for use with the atomizer of FIG. 18 according to an example embodiment of the present disclosure;

FIG. 25 illustrates a cross-section of the flow director of FIG. 24 according to an example embodiment of the present disclosure;

FIG. 26 illustrates a partial cross-section of the atomizer of FIG. 18 according to an example embodiment of the present disclosure;

FIG. 27 illustrates a different partial cross-section of the atomizer of FIG. 18 according to an example embodiment of the present disclosure; and FIG. 28 illustrates a partial front view of the cartridge of FIG. 23 according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of aerosol delivery devices. The aerosol delivery devices may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized as an electronic smoking article such as an electronic cigarette or "e-cigarette."

While the systems are generally described herein in terms of embodiments associated with aerosol delivery devices such as so-called "e-cigarettes," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery and/or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

One example embodiment of an aerosol delivery device 100 is illustrated in FIG. 1. In particular, FIG. 1 illustrates an aerosol delivery device 100 including a control body 200 and a cartridge 300. The control body 200 and the cartridge 300 can be permanently or detachably aligned in a functioning relationship. Various mechanisms may connect the cartridge 300 to the control body 200 to result in a threaded engagement, a press-fit engagement, an interference fit, a magnetic engagement, or the like. The aerosol delivery device 100 may be substantially rod-like, substantially tubular shaped, or substantially cylindrically shaped in some embodiments when the cartridge 300 and the control body 200 are in an assembled configuration. However, as noted above, various other configurations such as rectangular or fob-shaped may be employed in other embodiments. Further, although the aerosol delivery devices are generally described herein as resembling the size and shape of a traditional smoking article, in other embodiments differing configurations and larger capacity reservoirs, which may be referred to as "tanks," may be employed.

In specific embodiments, one or both of the cartridge 300 and the control body 200 may be referred to as being disposable or as being reusable. For example, the control body 200 may have a replaceable battery or a rechargeable battery and/or capacitor and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 300 may comprise a single-use cartridge, as disclosed in U.S. Pat. No. 8,910,639 to Chang et al., which is incorporated herein by reference in its entirety.

FIG. 2 illustrates an exploded view of the control body 200 of the aerosol delivery device 100 (see, FIG. 1) according to an example embodiment of the present disclosure. As illustrated, the control body 200 may comprise a coupler 202, an outer body 204, a sealing member 206, an adhesive member 208 (e.g., KAPTON® tape), a flow sensor 210 (e.g., a puff sensor or pressure switch), a control component 212, a spacer 214, an electrical power source 216 (e.g., a capacitor and/or a battery, which may be rechargeable), a circuit board with an indicator 218 (e.g., a light emitting diode (LED)), a connector circuit 220, and an end cap 222. Examples of electrical power sources are described in U.S. Pat. No. 9,484,155 to Peckerar et al., the disclosure of which is incorporated herein by reference in its entirety.

With respect to the flow sensor 210, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In one embodiment the indicator 218 may comprise one or more light emitting diodes. The indicator 218 can be in communication with the control component 212 through the connector circuit 220 and be illuminated, for example, during a user draw on a cartridge coupled to the coupler 202, as detected by the flow sensor 210. The end cap 222 may be adapted to make visible the illumination provided thereunder by the indicator 218. Accordingly, the indicator 218 may be illuminated during use of the aerosol delivery device 100 to simulate the lit end of a smoking article. However, in other embodiments the indicator 218 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

FIG. 3 illustrates the cartridge 300 of the aerosol delivery device 100 (see, FIG. 1) in an exploded configuration. As illustrated, the cartridge 300 may comprise a base 302, a control component terminal 304, an electronic component 306, a flow director 308, an atomizer 310, a reservoir 312 (e.g., a reservoir substrate), an outer body 314, a mouthpiece 316, a label 318, and first and second heating terminals 320, 321 according to an example embodiment of the present disclosure.

In some embodiments the first and second heating terminals 320, 321 may be embedded in, or otherwise coupled to, the flow director 308. For example, the first and second heating terminals 320, 321 may be insert molded in the flow director 308. Accordingly, the flow director 308 and the first and second heating terminals are collectively referred to herein as a flow director assembly 322. Additional description with respect to the first and second heating terminals 320, 321 and the flow director 308 is provided in U.S. Pat. Pub. No. 2015/0335071 to Brinkley et al., which is incorporated herein by reference in its entirety.

The atomizer 310 may comprise a liquid transport element 324 and a heating element 326. The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. Pat. No. 9,220,302 to Depiano et al., which is incorporated herein by reference in its entirety.

The base 302 may be coupled to a first end of the outer body 314 and the mouthpiece 316 may be coupled to an opposing second end of the outer body to substantially or fully enclose other components of the cartridge 300 therein. For example, the control component terminal 304, the electronic component 306, the flow director 308, the atomizer 310, and the reservoir 312 may be substantially or entirely retained within the outer body 314. The label 318 may at least partially surround the outer body 314, and optionally the base 302, and include information such as a product identifier thereon. The base 302 may be configured to engage the coupler 202 of the control body 200 (see, e.g., FIG. 2). In some embodiments the base 302 may comprise anti-rotation features that substantially prevent relative rotation between the cartridge and the control body as disclosed in U.S. Pat. App. Pub. No. 2014/0261495 to Novak et al., which is incorporated herein by reference in its entirety.

The reservoir 312 may be configured to hold an aerosol precursor composition. Representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Embodiments of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein. Additional description with respect to embodiments of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference in their entireties.

The reservoir 312 may comprise a plurality of layers of nonwoven fibers formed into the shape of a tube encircling the interior of the outer body 314 of the cartridge 300. Thus, liquid components, for example, can be sorptively retained by the reservoir 312. The reservoir 312 is in fluid connection with the liquid transport element 324. Thus, the liquid transport element 324 may be configured to transport liquid from the reservoir 312 to the heating element 326 via capillary action or other liquid transport mechanism.

As illustrated, the liquid transport element 324 may be in direct contact with the heating element 326. As further illustrated in FIG. 3, the heating element 326 may comprise a wire defining a plurality of coils wound about the liquid transport element 324. In some embodiments the heating element 326 may be formed by winding the wire about the liquid transport element 324 as described in U.S. Pat. No. 9,210,738 to Ward et al., which is incorporated herein by reference in its entirety. Further, in some embodiments the wire may define a variable coil spacing, as described in U.S. Pat. No. 9,277,770 to DePiano et al., which is incorporated herein by reference in its entirety. Various embodiments of materials configured to produce heat when electrical current is applied therethrough may be employed to form the heating element 326. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic).

However, various other embodiments of methods may be employed to form the heating element 326, and various other embodiments of heating elements may be employed in the atomizer 310. For example, a stamped heating element may be employed in the atomizer, as described in U.S. Pat. App. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various embodiments, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

The first heating terminal 320 and the second heating terminal 321 (e.g., negative and positive heating terminals) are configured to engage opposing ends of the heating element 326 and to form an electrical connection with the control body 200 (see, e.g., FIG. 2) when the cartridge 300 is connected thereto. Further, when the control body 200 is coupled to the cartridge 300, the electronic component 306 may form an electrical connection with the control body through the control component terminal 304. The control body 200 may thus employ the electronic control component 212 (see, FIG. 2) to determine whether the cartridge 300 is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on the mouthpiece 316 of the cartridge 300 of the aerosol delivery device 100 (see, FIG. 1). This may pull air through an opening in the control body 200 (see, e.g., FIG. 2) or in the cartridge 300. For example, in one embodiment an opening may be defined between the coupler 202 and the outer body 204 of the control body 200 (see, e.g., FIG. 2), as described in U.S. Pat. No. 9,220,302 to DePiano et al., which is incorporated herein by reference in its entirety. However, the flow of air may be received through other parts of the aerosol delivery device 100 in other embodiments. As noted above, in some embodiments the cartridge 300 may include the flow director 308. The flow director 308 may be configured to direct the flow of air received from the control body 200 to the heating element 326 of the atomizer 310.

A sensor in the aerosol delivery device 100 (e.g., the flow sensor 210 in the control body 200; see, FIG. 2) may sense the puff. When the puff is sensed, the control body 200 may direct current to the heating element 326 through a circuit including the first heating terminal 320 and the second heating terminal 321. Accordingly, the heating element 326 may vaporize the aerosol precursor composition directed to an aerosolization zone from the reservoir 312 by the liquid transport element 324. Thus, the mouthpiece 326 may allow passage of air and entrained vapor (i.e., the components of the aerosol precursor composition in an inhalable form) from the cartridge 300 to a consumer drawing thereon.

Various other details with respect to the components that may be included in the cartridge 300 are provided, for example, in U.S. Pat. App. Pub. No. 2014/0261495 to DePiano et al., which is incorporated herein by reference in its entirety. Additional components that may be included in the cartridge 300 and details relating thereto are provided, for example, in U.S. Pat. Pub. No. 2015/0335071 to Brinkley et al., filed May 23, 2014, which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In another embodiment substantially the entirety of the cartridge may be formed from one or more carbon materials, which may provide advantages in terms of biodegradability and absence of wires. In this regard, the heating element may comprise carbon foam, the reservoir may comprise carbonized fabric, and graphite may be employed to form an electrical connection with the power source and control component. An example embodiment of a carbon-based cartridge is provided in U.S. Pat. App. Pub. No. 2013/0255702 to Griffith et al., which is incorporated herein by reference in its entirety.

However, in some embodiments it may be desirable to provide aerosol delivery devices with alternative configurations. In this regard, FIG. 4 illustrates an aerosol delivery device 400 according to an example embodiment of the present disclosure. Where not otherwise described and/or illustrated, the components of the aerosol delivery device 400 may be substantially similar to, or the same as, corresponding components described above.

As illustrated, the aerosol delivery device may include a control body 200. The control body 200 may be similar to, or the same as the control body 200 described above (see, FIG. 2), and hence description thereof will not be repeated. However, in some embodiments the flow sensor 210 (see, FIG. 2) may comprise a microphone configured to detect a user draw on the cartridge 500. Further, other embodiments of the control body may be employed in the aerosol delivery device such as fob-shaped control bodies.

Further, the aerosol delivery device 400 may include a cartridge 500. The cartridge 500 may differ from the embodiment of the cartridge 300 described above with respect to FIGS. 1 and 3. In this regard, the cartridge 500 may not include an atomizer. Rather, the aerosol delivery device 400 may further comprise an atomizer body 600, which may include an atomizer, as described in detail below. Thus, whereas the aerosol delivery device 100 described above with respect to FIG. 1 includes two separable components (namely, the control body 200 and the cartridge 300), the aerosol delivery device 400 of FIG. 4 includes three separable components (namely, the control body 200, the cartridge 500, and the atomizer body 600).

More particularly, the control body 200 may be configured to releasably engage the atomizer body 600. Further, the atomizer body 600 may be configured to releasably engage the cartridge 500. As described hereinafter, the atomizer of the atomizer body 600 may be configured to receive an electrical current from the control body 200 and the aerosol precursor composition from the cartridge 500 to produce an aerosol.

FIG. 5 illustrates an exploded view of the cartridge 500. As illustrated, the cartridge 500 may include a reservoir 502 and a valve assembly 504. The reservoir 502 may be configured to contain an aerosol precursor composition 506. In some embodiments the reservoir 502 may comprise a translucent or transparent material, such that a user may view the quantity of the aerosol precursor composition 506 remaining therein. The aerosol precursor composition 506 may be dispensed or otherwise directed into the reservoir 502. For example, as illustrated in FIG. 6, a filling needle 508 may be directed into the reservoir 502 and the aerosol precursor composition 506 may be dispensed therefrom.

Thereafter, the valve assembly 504 may be inserted into the reservoir 502. The valve assembly 504 may seal the aerosol precursor composition 506 in the reservoir 502. Accordingly, the valve assembly 504 may retain the aerosol precursor composition 506 in the reservoir 502 without requiring usage of a reservoir substrate. However, as described hereinafter, the valve assembly 504 may allow the aerosol precursor composition 506 to flow to the atomizer body 600 when engaged therewith.

In some embodiments the valve assembly 504 may be affixed to the reservoir 504. For example, the valve assembly 504 may be ultrasonically welded to the reservoir 502. As may be understood, various other mechanisms and techniques such as usage of an adhesive may be employed to retain the valve assembly 504 in engagement with the reservoir 502. However, usage of ultrasonic welding may be preferable in that it may provide a hermetic seal without requiring an additional component or substance to form the seal. Thereby, nondestructive removal of the valve assembly 504 from the reservoir 502 may be prevented, such that the reservoir may not be refilled as described below in greater detail.

FIG. 7 illustrates an enlarged view of the valve assembly 504. As illustrated, the valve assembly 504 may include a frame 510. A base 512 of the frame 510 may be ultrasonically welded to an inner surface of the reservoir 502 to form the cartridge 500 (see, e.g., FIG. 5), as described above. Further, the frame 510 may include at least one connector portion 514, a first plate 516, a second plate 518, and at least one spacer 520. The connector portion 514 may extend from the base 512 to the first plate 516. The first plate 516 and the second plate 518 may be positioned adjacent to one another with a space defined therebetween. In this regard, the spacer 520 may extend between and separate the first plate 516 and the second plate 518 such that the first plate and the second plate are separated. A dispensing capillary tube 522 may extend through the first plate 516 to the space defined between the first plate and the second plate 518.

Further, the valve assembly 504 may include one or more seals. In particular, the valve assembly 504 may include a reservoir seal 524. The reservoir seal 524 may be configured to seal against the inside of the reservoir 502 to seal the aerosol precursor composition 506 in the reservoir (see, e.g., FIG. 5). The reservoir seal 524 may be molded to the frame 510 (e.g., insert molded).

Further, the valve assembly 504 may include a dispensing seal 526. The dispensing seal 526 may be positioned at the dispensing capillary tube 522. In particular, the dispensing seal 526 may be configured to seal the dispensing capillary tube 522 closed.

The reservoir seal 524 and/or the dispensing seal 526 may be molded to the frame 510. For example, the dispensing seal 526 and/or the reservoir seal 524 may be overmolded on the frame 510. By molding one or both of the seals 524, 526 to the frame 510, a strong bond may be formed therebetween that retains the seals in engagement with the frame.

In some embodiments the frame 510 may comprise a plastic material. An example commercially-available material that may be included in the frame 510 is TRITAN copolyester, sold by Eastman Chemical Company of Kingsport, Tenn. Further, in some embodiments the reservoir seal 524 and/or the dispensing seal 526 may comprise silicone, thermoplastic polyurethane, or other resilient material.

Regarding additional components of the aerosol delivery device 400 (see, FIG. 4), the atomizer body 600 is illustrated in a partially exploded configuration in FIG. 8. As illustrated, the atomizer body 600 may include an outer body 602. The outer body 602 may be configured to engage a base 604. For example, the outer body 602 may comprise a metal material (e.g., stainless steel), which may be crimped to the base 604, which may comprise a plastic material. When the outer body 602 is engaged with the base 604, various other components of the atomizer body 600 may be substantially enclosed therein.

For example, the atomizer body 600 may further comprise an atomizer 606. An example embodiment of the atomizer 606 is illustrated in FIG. 9. As illustrated, the atomizer 606 may comprise a liquid transport element 608 and a heating element 610. The liquid transport element 608 may comprise a porous monolith. For example, the liquid transport element 608 may comprise a ceramic.

The heating element 610 may comprise a wire, which may be coiled about the liquid transport element 608. In some embodiments the wire may comprise titanium, Kanthal (FeCrAl), Nichrome, Molybdenum disilicide (MoSi$_2$), molybdenum silicide (MoSi), Molybdenum disilicide doped with Aluminum (Mo(Si,Al)$_2$), graphite and graphite-based materials; ceramic (e.g., a positive or negative temperature coefficient ceramic), Tungsten, and Tungsten-based alloys, or any other suitable materials, such as those noted elsewhere herein. Usage of Tungsten and Tungsten-based alloys may be desirable in that these materials may define a coefficient of expansion suitable for usage with many ceramics, which may be employed in the liquid transport element 608.

The wire of the heating element 610 may be at least partially imbedded in the liquid transport element 608. In this regard, the wire of the heating element 610 may be imbedded in the liquid transport element 608 before the liquid transport element is fired in a high temperature oven known as a kiln. For example, the wire may be wrapped about a long section of the base material from which the ceramic is formed prior to firing the material. Examples of such base material employed to form the ceramic in the liquid transport element 608 may include clay, oxides, nonoxides, and composites. Thereby, the wire may at least partially imbed in the base material during wrapping thereabout. The base material and the wire may then be fired in the kiln. Afterwards, a gang saw or other cutting device may divide the product into individual atomizers 606 having a desired length.

The atomizer 606 may further comprise a capillary rod 612. In this regard, the liquid transport element 608 may define a tube. In other words, the liquid transport element 608 may include an aperture extending longitudinally therethrough. Thereby, the capillary rod 612 may extend longitudinally through the liquid transport element 608. As such, the capillary rod 612 may be configured to direct the aerosol precursor composition through the liquid transport element 608. In this regard, the spacing between the capillary rod 612 and the inner surface of the liquid transport element 608 may define a capillary channel that directs the aerosol precursor composition therethrough. The aerosol precursor composition may then be drawn generally radially outwardly through the liquid transport element 608 during activation of the heating element 610.

The atomizer body 600 (see, FIG. 4) may additionally include a first atomizer seal 614, which is illustrated in FIG. 9. The first atomizer seal 614 may engage a first end of the liquid transport element 608 and a first end of the capillary rod 612, which may define a head portion 616. Thereby, the liquid transport element 608 may be sealed to the head portion 616 of the capillary rod 612 to prevent leakage of the aerosol precursor composition therebetween.

FIG. 10 illustrates an exploded view of the base 604 and a plurality of terminals configured to engage the base. The terminals include a first heating terminal 618, a second heating terminal 620, and an electronic component terminal 622. The electronic component terminal 622 may be engaged with an electronic component 624 that verifies that the atomizer body 600 (see, e.g., FIG. 8) is genuine and/or provides other functions as described elsewhere herein.

The assembled configuration of the terminals 618, 620, 622 (see, FIG. 10) and the base 604 is illustrated in FIG. 11. As illustrated, the first heating terminal 620 may include a first clip 626. Further, the second heating terminal 620 may include a second clip 628.

As illustrated in FIG. 12, the first clip 626 and the second clip 628 may be aligned such that the liquid transport element 608 may be received therein and held in place. In this regard, the liquid transport element 608 may be inserted from a side through openings at each clip 626, 628 into engagement therewith. The first clip 626 and the second clip 628 may contact opposing ends of the heating element 610, such that current may be directed therethrough via the first heating terminal 618 and the second heating terminal 620. In some embodiments the clips 626, 628 may be welded (e.g., laser welded) to the heating element 610 to provide a secure connection therewith. For example, laser beams may be directed at each of the clips 626, 628, which may cause welds to form the clips and the heating element 610.

The atomizer body 600 (see, e.g., FIG. 4) may additionally include a second atomizer seal 630 and an atomizer body seal 632. As illustrated in FIG. 8, the atomizer body seal 632 may extend over the liquid transport element 608 and the heating terminals 618, 620 and into engagement with the base 604. As further illustrated in FIG. 8, the second atomizer seal 630 may be configured to engage the second end of the liquid transport element 608. Thereby the atomizer body seal 632 may extend over the liquid transport element 608 and the first and second heating terminals 618, 620 such that the liquid transport element cannot decouple from the first clip 626 (see, e.g., FIG. 12). Similar, the second atomizer seal 630 may extend over the liquid transport element 608 and the second heating terminal 620 such that the liquid transport element cannot decouple from the second clip 628 (see, e.g., FIG. 12). Accordingly, the liquid transport element 608 may remain in engagement with the heating terminals 618, 620.

Further, the second atomizer seal 630 and the atomizer body seal 632 may form seals. In this regard, the atomizer body seal 632 may seal against the base 604 and the outer body 602 when the outer body is engaged therewith. The second atomizer seal 630 and the atomizer body seal 632 may each engage inner surfaces of the outer body 602 to prevent leakage. In particular, the second atomizer seal 630 may engage an inner surface of the outer body 602 such that the aerosol precursor composition does not leak between the liquid transport element 608 and the outer body, but is instead directed through the longitudinal aperture defined through the liquid transport element.

Further, the atomizer body seal 632 may engage the inner surface of the outer body 602 and the base 604. Thereby, air may only enter the atomizer body 602 during a user draw through the base 604 through the atomizer body seal 632. In this regard, the atomizer body seal 632 may include one or more air flow apertures 634 configured to receive the air from the base 604 and direct the air to the outside of the atomizer 606. As discussed below, the aerosol produced at the atomizer 606 may then be directed out of the atomizer body 600 through the cartridge 500 (see, e.g., FIG. 4) to the user.

Operation of the aerosol delivery device 400 is described hereinafter in greater detail. As illustrated in FIG. 13, the atomizer body 600 may be engaged with the control body 200. Further, the cartridge 500 may be engaged with the atomizer body 600 such that the atomizer body is positioned between the control body and the cartridge 500. However, as may be understood, the atomizer body 600, the control body 200, and the cartridge 500 may be arranged differently in other embodiments.

The connection between the control body 200 and the atomizer body 600 via the first and second heating terminals 618, 620 and the electronic component terminal 622 (see, e.g., FIG. 10) allows the control body 200 to direct electrical current to the atomizer 606 when a puff on the aerosol delivery device 400 is detected. In this regard, a longitudinal end of the cartridge 500 opposite from the atomizer body 600 may define a mouthpiece 528. When the user draws on the mouthpiece 528, air 223 may be directed through an air intake 224, which may be defined between the coupler 202 and the outer body 204 of the control body 200. The air 223 drawn through the air intake 224 may be drawn through the coupler 202 of the control body 200 and then through the base 604 and the atomizer body seal 632 into an atomization cavity 638 of the atomizer body 600. Further, the air 223 may cool the electronic component 624 (see, e.g., FIG. 10) as it passes through the base 604 to reduce risk with respect to temperature-related degradation thereof.

The air 223 may be drawn through the air intake 224, as opposed to through the connection between the cartridge 500 and the atomizer body 600 due to inclusion of an O-ring 640 at an outer surface thereof, which may engage and seal against an inner surface of the reservoir 502 of the cartridge 500. Further, the reservoir 502 may define a detent 530 at an inner surface thereof that may engage a recess 642. Thereby, the atomizer body 600 may remain in secure engagement with the cartridge 500. To the extent any air enters the aerosol delivery device 400 between the control body 200 and the atomizer body 600, rather than through the air intake 224, this air may be combined with the air received through the air intake 224 at the atomization cavity 638.

The detent 530 and the recess 642 may additionally or alternatively provide other functions. In this regard, in some embodiments engagement of the detent 530 with the recess 642 may be required in order to allow for operation of the device. For example, engagement of the detent 530 with the recess 642 may complete a circuit with the electronic component 624 (see, e.g., FIG. 10), required for operation of the aerosol delivery device.

As the air is drawn through the air intake 224, the flow sensor 210 (see, FIG. 2) may detect the draw. Thereby, the control body 200 may direct current through the heating terminals 618, 620 to the atomizer 606. As the atomizer 606 heats, the aerosol precursor composition 506 may be vaporized at the atomizer. In this regard, the aerosol precursor composition 506 may be retained in a precursor cavity 532 in the reservoir 502. The aerosol precursor composition 506 may be directed through the valve assembly 504 to the atomizer 606.

In this regard, the valve assembly 504 may be configured to dispense the aerosol precursor composition 506 to the atomizer body 600 when engaged therewith. At other times the valve assembly 504 may remain in a closed configuration so as to retain the aerosol precursor composition 506 in the reservoir 502. More particularly, the atomizer body 600 may include a nozzle 644. The nozzle 644 may be configured to engage the valve assembly 504. In this regard, the nozzle 644 may be configured to extend through the reservoir seal 524 and engage the dispensing seal 526. Accordingly, the aerosol precursor composition 506 retained in the precursor cavity 532 may be directed through the valve assembly 504 to the nozzle 644.

As illustrated in FIGS. 14 and 15, the aerosol precursor composition 506 may flow through a gap defined between the radial outer edges of the first plate 516 and the second plate 518 of the valve assembly 504 and an inner surface of the reservoir 502 and into a space defined between the first plate and the second plate. More particularly, FIG. 15 illustrates an enlarged view of area Z from FIG. 14. As illustrated, capillary action may draw the aerosol precursor composition 506 between the first plate 516 and the second plate 518.

In some embodiments internal surfaces of the first plate 516 and the second plate 518 may define an angle with respect to each other. In particular, the first plate 516 and the second plate 518 may be shaped and configured such that the internal surfaces are furthest from one another proximate the outer edges thereof, and closest to one another proximate the dispensing capillary tube 522. Thereby a distance between the first plate 516 and the second plate may decrease from the outer edges of the plates towards the centers thereof. For example, the inner surfaces of the first plate 516 and the second plate 518 may define an angle with respect to one another, which may be between about 1 degrees and about 5 degrees in some embodiments. By configuring the first plate 516 and the second plate 518 in this manner, a "draft" may be created, which draws the aerosol precursor composition toward the dispensing capillary tube 522. Accordingly, the aerosol precursor composition may be drawn into the dispensing capillary tube 522 (see, e.g., FIG. 13) defined through the first plate, such that flow of the aerosol precursor composition thereto may occur in any orientation in which the aerosol precursor composition contacts the first plate 516 and the second plate 518. Further, an entrained volume of the aerosol precursor composition 506 in the valve assembly 504 and downstream components may allow for continued operation in any orientation (e.g., about fifteen to twenty puffs) before the orientation of the aerosol delivery device 400 (see, e.g., FIG. 13) would need to be changed to one in which the aerosol precursor composition contacts the first plate 516 and the second plate 518.

Further, the dispensing seal may seal against the nozzle 644. This may isolate a nozzle orifice at an end of the nozzle 644 in order to draw aerosol precursor composition from the fluid volume between the first plate 516 and the second plate 518. This configuration operates as a thermal pump, providing additional efficiency in the transport of the aerosol precursor composition and more efficient extraction of substantially all of the aerosol precursor composition from the precursor cavity 532. In other words, this design is configured to allow substantially complete consumption of the aerosol precursor composition contain such that the cartridge 500 can be run "dry," such that the consumer does not perceive any residual aerosol precursor composition left in the precursor cavity 532.

Thereby, as illustrated in FIG. 13, the aerosol precursor composition 506 may be directed through the nozzle 644 into the liquid transport element 608. The aerosol precursor composition 506 may then be vaporized by the heating element 610 directly or via heating of the liquid transport element 608. Accordingly, the resultant vapor or aerosol 646 may be produced at the atomization cavity 638 and then be directed to the user. In this regard, the outer body 602 of the atomizer unit 600 may include one or more air flow apertures 648 extending therethrough and in fluid communication with the atomization cavity 638. Further, one or more air flow apertures 534 may be defined through the reservoir seal 524 of the valve assembly 504 and align with the air flow apertures 648 extending through the outer body 602 of the atomizer unit 600.

Additionally, the reservoir 502 may include one or more air flow apertures 536 extending from the valve assembly 504 to the mouthpiece 528. The air flow apertures 536 extending through the reservoir 502 may be separated from the precursor cavity 532 in which the aerosol precursor composition 506 is received. In this regard, the air flow apertures 536 may be defined through the material forming the reservoir 502 circumferentially about the precursor cavity 532. Accordingly, the aerosol 646 may be directed from the atomization cavity 638 through the mouthpiece 528 to the user.

As described above with reference to FIG. 13, the cartridge 500 may include the aerosol precursor composition 506 and the atomizer body 600 may include the atomizer 606. By allowing for replacement of the cartridge 500 without requiring replacement of the atomizer 606 at the same time, the cost associated with usage of the aerosol delivery device 400 may be reduced. In this regard, in some embodiments the atomizer 606 may have a useable life configured to atomize a quantity of aerosol precursor composition 506 contained in about two hundred to about three hundred cartridges 500 before requiring replacement.

In contrast, the cartridge 500 may be configured to be discarded after the aerosol precursor composition 506 is depleted therefrom. In this regard, the cartridge 500 may be configured to prevent refilling thereof. FIG. 16 illustrates a view of the cartridge 500 at the valve assembly 504. As illustrated, the reservoir seal 524 may define an orifice 538 configured to guide and receive the nozzle 644 of the atomizer body 600 (see, e.g., FIG. 13), as described above. As may be understood, a user may attempt to employ the orifice 538 to refill the reservoir 502 with aerosol precursor composition. However, the valve assembly 504 may be configured to resist refilling.

In this regard, the frame 510 may include one or more protrusions 540 that extend outwardly from the reservoir seal 524. In some embodiments the protrusions 540 may be defined by the connector portions 514 (see, FIG. 7) of the frame 510. As a result of the protrusions 540 protruding outwardly from the reservoir seal 524, a bottle nozzle or glass dripper may not be able to form a face seal with respect to the reservoir seal, which may be required to allow flow of fluid through the reservoir seal. In this regard, the reservoir seal 524 and the dispensing seal 526 (see, FIG. 7) may define valves that are closed in an unbiased configuration and which open during engagement with the nozzle 644 when the cartridge 500 engages the atomizer body 600 (see, e.g., FIG. 13). As a result of resisting the formation of seal with respect to most bottle nozzles and glass drippers, the reservoir seal 524 may thereby resist refilling of the reservoir 502.

Further, by employing two or more of the protrusions 540 around the orifice 538, a width of any nozzle that may engage the orifice 538 may be restricted to further limit the type of nozzle that may extend through the orifice and/or form a face seal therewith. In some embodiments the orifice may define a diameter from about one millimeter to about three millimeters, which may be too small for standard e-liquid bottle nozzles or glass dropper tips to be inserted therein. Further, usage of both the reservoir seal 524 and the dispensing seal 526, each formed from a resilient material and separated from one another, may make it difficult to employ a hypodermic needle to refill the reservoir 502.

Attempts to refill the cartridge 500 by forming a seal with an inner surface of the base 512 of the frame 510 to refill the reservoir 502 may also fail. In this regard, the air flow apertures 534 defined in the reservoir seal 524 would allow aerosol precursor composition to flow out of the cartridge 500 through the air flow apertures 536 (see, FIG. 13) defined in the reservoir 502, thereby resisting refilling of the reservoir 502.

Additionally, as noted above, the valve assembly 504 may be recessed in and affixed to the reservoir 502 (e.g., via ultrasonic welding). As such, the valve assembly 504 may not be removed from the reservoir 502 without damaging one or both of these components, thereby further resisting refilling of the cartridge 500). Additionally, in view of the atomizer 606 being included in a separate atomizer body 600 (see, e.g., FIG. 13) instead of in the cartridge 500, the cartridge may be priced relatively more inexpensively, which may mitigate cost savings as a driving factor for a user attempting to refill the cartridge.

In an additional embodiment an aerosol delivery device operation method is provided. As illustrated in FIG. 17, the method may include directing an aerosol precursor composition from a reservoir of a cartridge out of the cartridge through a valve assembly at operation 702. Directing the aerosol precursor composition from the reservoir of the cartridge out of the cartridge through the valve assembly at operation 702 may include directing the aerosol precursor composition through a dispensing capillary tube, a dispensing seal at the dispensing capillary tube and a reservoir seal at the reservoir. Further, the method may include receiving the aerosol precursor composition in an atomizer body at operation 704. The method may additionally include directing the aerosol precursor composition to an atomizer in the atomizer body at operation 706. The method may further include directing an electrical current from a control body to the atomizer to produce an aerosol at operation 708.

In some embodiments directing the aerosol precursor composition out of the cartridge through the valve assembly at operation 702 may further include directing the aerosol precursor composition between a first plate and a second plate positioned adjacent to one another with a space defined therebetween and out of the space through the dispensing capillary tube extending through the first plate. Directing the aerosol precursor composition out of the cartridge through the valve assembly at operation 702 may further include engaging a nozzle of the atomizer body with the valve assembly. Engaging the nozzle with the valve assembly may include directing the nozzle through the reservoir seal of the valve assembly. Engaging the nozzle with the valve assembly may further include engaging the nozzle with the dispensing seal of the valve assembly at the dispensing capillary tube.

In some embodiments receiving the aerosol precursor composition in the atomizer body at operation 704 comprises directing the aerosol precursor composition between the nozzle and a capillary rod. Directing the aerosol precursor composition to the atomizer in the atomizer body at operation 706 may include directing the aerosol precursor composition between the capillary rod and a liquid transport element of the atomizer. The method may further include directing the aerosol through one or more air flow apertures extending through the cartridge. Directing the aerosol through one or more air flow apertures extending through the cartridge may include directing the aerosol through the valve assembly.

As may be understood, the apparatuses and method of the present disclosure may vary. In this regard, FIG. 18 illustrates a cartridge 800 and an atomizer 900 according to an additional example embodiment of the present disclosure. In particular, FIG. 18 illustrates the cartridge 800 and the atomizer 900 in an assembled configuration, and engaged with one another. The atomizer 900 may be configured to engage a control body such as the control body 200 (see, e.g., FIG. 2) described above. It should be noted that with regard to this embodiment, the atomizer 900 may also comprise the atomizer body and thus the terms atomizer and atomizer body may be used interchangeably. Where not otherwise described and/or illustrated, the components of an aerosol delivery device according to this embodiment may be substantially similar to, or the same as, corresponding components described above.

FIGS. 19 and 20 illustrate the atomizer 900 by itself. FIG. 19 illustrates the atomizer 900 in an assembled configuration (minus a label 902), whereas FIG. 20 illustrates the atomizer body in an exploded configuration. As illustrated, the atomizer 900 may include the label 902, a base 904, an atomizer air valve 906, a terminal base 908, a first heating terminal 910, a second heating terminal 912, a liquid transport element 914, a flow director 916, an outer o-ring 918, and an outer body 920. As illustrated in FIG. 19, the outer body 920 may include a nozzle 922 and a plurality of vapor apertures 924.

In various embodiments, a control body may be configured to releasably engage the atomizer 900. Further, the atomizer 900 may be configured to releasably engage the cartridge 800. As described hereinafter, the atomizer 900 may be configured to receive an electrical current from the control body and the aerosol precursor composition from the cartridge 800 to produce an aerosol.

Referring to FIG. 20, the atomizer 900 may also include a terminal base 908. In various embodiments, the terminal base may be constructed of a plastic material, including, but not limited to, a silicone, a thermoplastic polyurethane, or another resilient material. An example commercially-available material that may be used for the terminal base is TRITAN copolyester, sold by Eastman Chemical Company of Kingsport, Tenn. In the illustrated embodiment, the first heating terminal 910 and the second heating terminal 912 pass through the terminal base 908. In various embodiments, the first heating terminal 910 and the second heating terminal 912 may be inserted molded within the terminal base 908. In such a manner, the terminal base 908 may comprise an overmold with the first heating terminal 910 and the second heating terminal 912 fixedly attached therein.

FIGS. 21 and 22 illustrate separate views of the cartridge 800. As illustrated, the cartridge 800 may include an internal reservoir 802 and a central passageway 804. The cartridge may also include a dispensing valve 806 and a substantially circular vapor flow groove 808 defined in a bottom surface of the cartridge 800 that leads to a pair of vertical cartridge vapor channels 810. As with the embodiments described above, the reservoir 802 may be configured to contain an aerosol precursor composition. In some embodiments the cartridge 800 may comprise a translucent or transparent material, such that a user may view the quantity of the aerosol precursor composition remaining therein. The aerosol precursor composition may be dispensed or otherwise directed into the reservoir 802. The valve 806 may seal the aerosol precursor composition in the reservoir 802. However, as described hereinafter, the valve 806 may allow the aerosol precursor composition to flow to the atomizer 900 when engaged therewith.

FIG. 23 illustrates an example embodiment of the liquid transport element 914. Also shown are a heating element 926 for use with the atomizer 900, the first heating terminal 910, and the second heating terminal 912. Note that to simply the figure, the terminal base 908 is not shown. In various embodiments, the liquid transport element 914 may comprise a porous monolith. For example, the liquid transport element 608 may comprise a ceramic. As illustrated, the heating element 926 may comprise a wire, which may be coiled about an inside surface of the liquid transport element 914. In some embodiments, the wire may comprise titanium, Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; ceramic (e.g., a positive or negative temperature coefficient ceramic), Tungsten, and Tungsten-based alloys, or any other suitable materials, such as those noted elsewhere herein. Usage of Tungsten and Tungsten-based alloys may be desirable in that these materials may define a coefficient of expansion suitable for usage with many ceramics, which may be employed in the liquid transport element 914.

The wire of the heating element 926 may be at least partially imbedded in the liquid transport element 914. In this regard, the wire of the heating element 926 may be imbedded in the liquid transport element 914 before the liquid transport element is fired in a high temperature oven known as a kiln. In various embodiments, the first heating terminal 910 contacts one end of the heating element 926 and the second heating terminal 912 contacts another end of the heating element 926, such that an electric current can be passed through the heating element 926.

As noted above, in some embodiments, thermally coupling of the heating element 926 to the liquid transport element 914 may occur via embedding or partially embedding the heating element 926 in the liquid transport element 914. In other embodiments, thermally coupling the heating element to the liquid transport element may occur via "direct writing," which may comprise computer aided surface deposition of specialized alloyed flowable metals to a substrate. In other embodiments, the heating element may be coupled to the liquid transport element via plating, electroplating, direct deposition (e.g., sputtering), and/or other suitable methods.

As also shown in FIG. 23, in various embodiments, the liquid transport element 914 may include an external electrical connection 927, which may be the external component of the electrical pathway between the heating terminals 910 and 912 and the heating element 926. In the depicted embodiment, the external electrical connection 927 comprises a helical coil in and/or on the outer surface of the liquid transport element 914. In various embodiments, the external electrical connection may have functional characteristics with regard to the thermal performance of the heating element and liquid transport element. As with the heating element described above, the external electrical connection may be a directly written or partially embedded element.

In some embodiments, it may be desirable to decrease thermal transfer from the heating element to the device (most directly via the atomizer housing) and therefor the user, and/or to decrease thermal degradation of the device (as discussed in this draft in regards to air cooling of electrical components), and/or to increase the efficiency of the heat generated by the heating element and applied to the aerosol precursor composition to effect mass transfer of precursor to aerosol or vapor (with associated efficiency benefits such as decreased power consumption and increased overall system efficiency). Thus, in some embodiments, the external electrical connection may be comprised of a material dissimilar in thermal conductivity to that of the liquid transport element, thus creating a thermal gradient across the liquid transport element with greater thermal conductivity across the internal surface of the liquid transport element than the external surface.

In some embodiments, the mass of the material could also be utilized to effect an increased differential of the time delta for heat transfer through the liquid transport element. In addition, many processes including direct writing and those mentioned above can by utilized to selectively alter the characteristics of the liquid transport element. In addition, the application of concurrent or post-firing processes that "dope" the surface of the material and can penetrate to selected depths of the substrate depending on substrate porosity, material composition, process and application are possible approaches. In various embodiments, conductive non-porous ceramic based materials could also be utilized for the liquid transport element. In this regard, a thermal gradient may exist across the cross-section of the liquid transport element, with a substantially hotter area across the internal surface of the liquid transport element to effect phase transition and mobilization of the precursor composition, with the external surface of the liquid transport element remaining relatively cooler serving to insulate and isolate the heat to the atomization chamber.

Alternatively, it may be desirable to simply insulate the direct region of the external electrical connection that makes connection with the first and second heating terminals. In such embodiments, the external electrical connection could also serve as a restive heater itself. In this capacity, the external electrical connection and the heating element may have dissimilar resistance characteristics such that the external electrical connection may help to overcome an initial thermal ramp required in the initial heating phase of a user activation process. In such embodiments, the external electrical connection may not reach temperatures required for mobilization of the precursor. Rather, the external electrical connection may heat to a lower temperature than that of the heating element. This could increase vapor product over time by decreasing the time delta from activation to aerosol generation. In this capacity the external electrical connection may also warm the proximate precursor located in and adjacent to the liquid transport element by decreasing the viscosity of the precursor, facilitating increased transport to the liquid transport element.

FIG. 24 illustrates an isometric view of the flow director 916 for use with the atomizer 900. FIG. 25 illustrates a cross-sectional view of the flow director 916. In various embodiments, the flow director 916 may generally have a "T" shape that includes an upper flange 925 and a lower cylinder 927. The flow director further includes a central inlet air channel 928, a series of inlet air holes 930, a transition barrier 931, and a series of inlet vapor holes 932. The inlet vapor holes 932 lead to a series of radial vapor channels 934 located in the upper flange 925, which each leads to a vertical vapor hole 936. The flow director also includes a series of inlet liquid flow channels 938 located on the upper flange 925, which, when assembled with the liquid transport element 914, abut a top surface thereof. It should be noted that although the distal ends of the radial vapor channels shown in FIG. 25 appear to extend through holes in an outer surface of the upper flange 925, in such embodiments, these holes are sealed or otherwise occluded so as to create a direct flow path though the radial vapor channels 934 and into the vertical vapor holes 936 (see FIG. 26). In other embodiments, the radial vapor channels may terminate at the vertical vapor holes, such that there are no openings along the outer surface of the upper flange.

Operation of an example embodiment of an aerosol delivery device is described hereinafter in greater detail. As noted above, the atomizer 900 may be engaged with the control body 200, and, as illustrated in FIGS. 26 and 27 the cartridge 800 may be engaged with the atomizer 900 such that the atomizer 900 is positioned between the control body 200 and the cartridge 800. However, as may be understood, the atomizer 900, the control body 200, and the cartridge 800 may be arranged differently in other embodiments.

In this regard, when the cartridge 800 is coupled to the atomizer 900 and control body 200, the nozzle 922 of the atomizer 900 may be configured to engage with the dispensing valve 806 of the cartridge 800. In such a manner, the aerosol precursor composition 506 may flow through the cartridge 800 and into the nozzle 922 of the outer body 920 of the atomizer 900. Due to the relative position of the flow director 916 when coupled with the outer body 920 and via capillary action, the aerosol precursor composition 506 may be drawn through a series of radial flow openings 940 onto the top of the upper flange 925 of the flow director 916 (see FIG. 26). From there, the aerosol precursor composition may be drawn through the inlet liquid flow channels 938 that extend vertically through the upper flange 925 of the flow director 916, and onto the top surface of the liquid transport element 914 (see FIG. 27). In such a manner, an atomizer chamber 942 is created on the inside of the liquid transport element 914, bounded by the flow director 916 and the terminal base 908. In some embodiments, the aerosol precursor composition may be drawn through the inlet liquid flow channels 938 onto an outside surface of the liquid transport element 914 in addition to or instead of the top surface of the liquid transport element 914.

A connection between the control body 200 and the atomizer 900 via the first and second heating terminals 910, 912 allows the control body 200 to direct electrical current to the atomizer 900 when a puff on the aerosol delivery device 400 is detected. In this regard, a longitudinal end of the cartridge 800 opposite from the atomizer 900 may define a mouthpiece. When the user draws on the mouthpiece, air 223 may be directed through the atomizer base 904 and the atomizer air valve 906, and into the central inlet air channel 928 of the flow director 916. In particular, as the air is drawn into the aerosol delivery device, the flow sensor 210 (see, FIG. 2) may detect the draw. Thereby, the control body 200 may direct current through the heating terminals 910, 912 to the atomizer 900. In some embodiments, the upstream air 223 may cool an electronic component before it flows into the central air channel 928 to reduce risk with respect to temperature-related degradation thereof. As the atomizer 900 heats, the aerosol precursor composition 506 may be vaporized by the heating element 926 via heating of the liquid transport element 914, which absorbs the aerosol precursor composition 506 therein. Accordingly, the resultant vapor or aerosol 646 may be produced on the inside surface of the liquid transport element 914 and/or within the atomizer chamber 942.

When the air 223 flows through the central inlet air channel 928, it is directed through the series of first inlet air holes 930 of the lower cylinder 927 by the transition barrier 931 (see FIG. 26) and into the atomizer chamber 942 (i.e., past the inside surface of the liquid transport element 914) where it becomes the vapor or aerosol 646. Due to the geometry and relative arrangement of the flow director 916 and the outer body 920, including a diverting feature 933 of the outer body 920, which is configured to fit into and occlude the central opening in the top of the flow director 916, the resultant vapor or aerosol 646 travels through the series of radial vapor channels 934 in the upper flange 925 of the flow director 916, up through the series of vertical vapor holes 932, and through at least some of the plurality of vapor apertures 924 in the outer body 920.

It should be noted that the "tortuous path" of the aerosol through the upper flange 925 of the flow director 916 via the inlet vapor holes 932, radial vapor channels 934, and vertical vapor holes 936, may have the functional roll of creating a series of impaction surfaces configured to capture aerosol droplets outside of (i.e., larger) an optimal range. In such a manner, droplets having a greater mass may not remain entrained in the airflow as the path makes 90 degree turns through the inlet vapor holes 932, the radial vapor channels 934, and the vertical vapor holes 936 and may thus impact within the upper flange 925, where they may drain back into the atomizer chamber 942.

FIG. 28 shows the flow of the vapor or aerosol 646 through the cartridge 800, leading to the central passageway 804. When the cartridge 800 is coupled to the atomizer 900, the circular vapor flow groove 808 of the cartridge 800 is configured to substantially align with the plurality of vapor apertures 924 of the outer body 920 of the atomizer 900. As such, vapor or aerosol 646 flowing through the plurality of vapor apertures 924 may be directed by the vapor flow groove 808 into the vertical cartridge vapor channels 810. As shown in the figure, the vertical vapor channels 810 lead to respective horizontal vapor channels 812, which then lead to the central passageway 804 of the cartridge 800.

As described above with reference to additional implementations, the cartridge 800 may include the aerosol precursor composition 506. By allowing for replacement of the cartridge 800 without requiring replacement of the atomizer 900 at the same time, the cost associated with usage of the aerosol delivery device may be reduced. In this regard, in some embodiments the atomizer 900 may have a useable life configured to atomize a quantity of aerosol precursor composition 506 contained in about two hundred to about three hundred cartridges 800 before requiring replacement.

In contrast, the cartridge 900 may be configured to be discarded after the aerosol precursor composition 506 is depleted therefrom. In this regard, the cartridge 800 may be configured to prevent refilling thereof as similarly described with respect to the embodiments illustrated above. For example, FIG. 22 illustrates a bottom view of the cartridge 800. As illustrated, the dispensing valve 806 may define an orifice 814 configured to guide and receive the nozzle 922 of the atomizer 900, as described above. As may be understood, a user may attempt to refill the reservoir 802 with aerosol precursor composition; however, the cartridge 800 may be configured to resist refilling.

In this regard, the cartridge 800 may include one or more protrusions 816 that extend inwardly from an area proximate the vapor flow groove 808, toward the dispensing seal 806. As a result of the protrusions 816 protruding inwardly toward the dispensing seal 806, a bottle nozzle or glass dripper may not be able to form a face seal with respect to the dispensing seal, which may be required to allow flow of fluid through the dispensing seal. In this regard, the dispensing seal 806 may define a valve that is closed in an unbiased configuration and which open during engagement with the nozzle 922 when the cartridge 800 engages the atomizer 900. As a result of resisting the formation of seal with respect to most bottle nozzles and glass drippers, the dispensing seal 806 may thereby resist refilling of the reservoir 802. Further, by employing two or more of the protrusions 816 around the orifice 814, a width of any nozzle that may engage the orifice 806 may be restricted to further limit the type of nozzle that may extend through the orifice and/or form a face seal therewith. In some embodiments the orifice may define a diameter from about one millimeter to about three millimeters, which may be too small for standard e-liquid bottle nozzles or glass dropper tips to be inserted therein.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
   a control body;
   an atomizer body comprising an atomizer; and
   a cartridge, comprising:
      a reservoir configured to contain an aerosol precursor composition; and
      a valve assembly configured to dispense the aerosol precursor composition to the atomizer body when the cartridge is engaged with the atomizer body, the valve assembly including a dispensing seal and a reservoir seal,
   the control body being configured to releasably engage the atomizer body and the atomizer body being configured to releasably engage the cartridge,
   the atomizer being configured to receive an electrical current from the control body and the aerosol precursor composition from the cartridge to produce an aerosol,
   wherein the control body, the atomizer body, and the cartridge comprise separate components.

2. The aerosol delivery device of claim 1, wherein the cartridge comprises one or more air flow apertures extending from the atomizer body to a mouthpiece, the air flow apertures being configured to direct the aerosol therethrough.

3. The aerosol delivery device of claim 2, wherein at least one of the air flow apertures extends through the valve assembly.

4. An aerosol delivery device, comprising:
   a control body;
   an atomizer body comprising an atomizer; and
   a cartridge, comprising:
      a reservoir configured to contain an aerosol precursor composition; and
      a valve assembly configured to dispense the aerosol precursor composition to the atomizer body when the cartridge is engaged with the atomizer body, the valve assembly including a dispensing seal and a reservoir seal,
   the control body being configured to releasably engage the atomizer body and the atomizer body being configured to releasably engage the cartridge,
   the atomizer being configured to receive an electrical current from the control body and the aerosol precursor composition from the cartridge to produce an aerosol,
   wherein the valve assembly defines a dispensing capillary tube, and wherein the valve assembly further comprises a first plate and a second plate positioned adjacent to one another with a space defined therebetween, the dispensing capillary tube extending through the first plate to the space between the first plate and the second plate.

5. The aerosol delivery device of claim 4, wherein a gap is defined between a radial outer edge of the first plate and a radial outer edge of the second plate and an inner surface of the reservoir.

6. The aerosol delivery device of claim 1, wherein the atomizer body further comprises a nozzle configured to extend through the reservoir seal and engage the dispensing seal.

7. The aerosol delivery device of claim 1, wherein the valve assembly further comprises a frame and the reservoir seal is molded to the frame.

8. The aerosol delivery device of claim 1, wherein the atomizer comprises a liquid transport element comprising a porous monolith.

9. The aerosol delivery device of claim 8, wherein the atomizer further comprises a heating element comprising a wire at least partially imbedded in the liquid transport element.

10. The aerosol delivery device of claim 9, wherein the liquid transport element defines a tube and the atomizer further comprises a capillary rod extending through the liquid transport element and configured to direct the aerosol precursor composition therethrough.

11. The aerosol delivery system of claim 1, wherein the control body further comprises a microphone, the microphone being configured to detect a user draw on the cartridge.

12. An aerosol delivery device, comprising:
a control body;
an atomizer body comprising an atomizer; and
a cartridge, comprising:
a reservoir configured to contain an aerosol precursor composition; and
a valve assembly configured to dispense the aerosol precursor composition to the atomizer body when the cartridge is engaged with the atomizer body, the valve assembly including a dispensing seal and a reservoir seal,
the control body being configured to releasably engage the atomizer body and the atomizer body being configured to releasably engage the cartridge,
the atomizer being configured to receive an electrical current from the control body and the aerosol precursor composition from the cartridge to produce an aerosol,
wherein the atomizer comprises an outer body, a terminal base, a flow director, and a liquid transport element comprising a porous monolith, and wherein an atomizer chamber is created by the flow director, the terminal base, and an inside surface of the liquid transport element.

13. The aerosol delivery system of claim 12, wherein the flow director includes a central inlet air channel, a transition barrier, and one or more radial inlet air holes configured such that air that enters through the inlet air channel is directed through the one or more radial inlet air holes by the transition barrier.

14. The aerosol delivery system of claim 13, wherein the flow director further includes one or more inlet liquid flow chambers configured to deliver the aerosol precursor composition to the liquid transport element.

15. The aerosol delivery system of claim 14, wherein the outer body includes one or more vapor apertures, and the flow director further includes one or more radial inlet vapor holes, one or more radial vapor channels, and one or more vertical vapor holes, configured such that the aerosol is directed through the one or more radial inlet vapor holes, the one or more radial vapor channels, the one or more vertical vapor holes of the flow director, and the one or more vapor apertures of the outer body and into one or more vapor channels of the cartridge.

16. An aerosol delivery device operation method, comprising:
directing an aerosol precursor composition from a reservoir of a cartridge out of the cartridge through a valve assembly by directing the aerosol precursor composition through a dispensing seal and a reservoir seal at the reservoir;
receiving the aerosol precursor composition in an atomizer body;
directing the aerosol precursor composition to an atomizer in the atomizer body; and
directing an electrical current from a control body to the atomizer to produce an aerosol,
wherein the valve assembly defines a dispensing capillary tube, and wherein directing the aerosol precursor composition out of the cartridge through the valve assembly further comprises directing the aerosol precursor composition between a first plate and a second plate positioned adjacent to one another with a space defined therebetween and out of the space through the dispensing capillary tube extending through the first plate.

17. The aerosol delivery device operation method of claim 16, wherein directing the aerosol precursor composition out of the cartridge through the valve assembly further comprises engaging a nozzle of the atomizer body with the valve assembly.

18. The aerosol delivery device operation method of claim 17, wherein engaging the nozzle with the valve assembly comprises directing the nozzle through the reservoir seal of the valve assembly.

19. The aerosol delivery device operation method of claim 18, wherein engaging the nozzle with the valve assembly further comprises engaging the nozzle with the dispensing seal of the valve assembly at the dispensing capillary tube.

20. The aerosol delivery device operation method of claim 17, wherein receiving the aerosol precursor composition in the atomizer body comprises directing the aerosol precursor composition between the nozzle and a capillary rod.

21. The aerosol delivery device operation method of claim 20, wherein directing the aerosol precursor composition to the atomizer in the atomizer body comprises directing the aerosol precursor composition between the capillary rod and a liquid transport element of the atomizer.

22. The aerosol delivery device operation method of claim 16, further comprising directing the aerosol through one or more air flow apertures extending through the cartridge.

23. The aerosol delivery device operation method of claim 22, wherein directing the aerosol through one or more air flow apertures extending through the cartridge includes directing the aerosol through the valve assembly.

24. An aerosol delivery device operation method, comprising:
directing an aerosol precursor composition from a reservoir of a cartridge out of the cartridge through a valve assembly by directing the aerosol precursor composition through a dispensing seal and a reservoir seal at the reservoir;
receiving the aerosol precursor composition in an atomizer body;

directing the aerosol precursor composition to an atomizer in the atomizer body; and directing an electrical current from a control body to the atomizer to produce an aerosol, wherein directing the aerosol precursor composition to an atomizer in the atomizer body comprises directing the aerosol precursor composition through one or more radial flow openings in an outer body of the atomizer and through one or more inlet liquid flow channel in a flow director of the atomizer.

25. The aerosol delivery operation method of claim 24, further comprising directing the aerosol through one or more radial inlet vapor holes, one or more radial vapor channels, and one or more vertical vapor holes of the flow director, one or more vapor apertures of an outer body of the atomizer, and into one or more vapor channels of the cartridge.

* * * * *